US008728754B1

(12) United States Patent
Huang et al.

(10) Patent No.: US 8,728,754 B1
(45) Date of Patent: May 20, 2014

(54) USE OF PROTEINS ISOLATED FROM PSEUDOMONAS TO CONTROL MOLLUSCS

(71) Applicant: Marrone Bio Innovations, Inc., Davis, CA (US)

(72) Inventors: Huazhang Huang, Woodland, CA (US); Ratnakar Asolkar, Davis, CA (US); Pamela Marrone, Davis, CA (US); Ana Lucia Cordova-Kreylos, Davis, CA (US)

(73) Assignee: Marrone Bio Innovations, Inc., Davis, CA (US)

(*) Notice: Subject to any disclaimer, the term of this patent is extended or adjusted under 35 U.S.C. 154(b) by 0 days.

(21) Appl. No.: 13/837,353

(22) Filed: Mar. 15, 2013

Related U.S. Application Data

(60) Provisional application No. 61/755,969, filed on Jan. 23, 2013.

(51) Int. Cl.
 C12Q 1/32 (2006.01)
 A61K 38/00 (2006.01)
 A61K 38/54 (2006.01)

(52) U.S. Cl.
 USPC ............................ 435/26; 424/94.5; 424/94.2

(58) Field of Classification Search
 USPC .................................. 435/26; 424/94.5, 94.2
 See application file for complete search history.

(56) References Cited

U.S. PATENT DOCUMENTS

| 4,542,097 A | 9/1985 | Labows, Jr. et al. |
| 4,560,656 A | 12/1985 | Farbood et al. |
| 5,527,525 A | 6/1996 | Wilson et al. |
| 6,194,194 B1 | 2/2001 | Molloy |
| 6,451,565 B1 | 9/2002 | Rabenhorst et al. |
| 7,129,067 B2 | 10/2006 | Mitsuhashi et al. |
| 2004/0234629 A1 | 11/2004 | Nakazato et al. |
| 2010/0266717 A1 | 10/2010 | Asolkar et al. |
| 2011/0021358 A1 | 1/2011 | Huang et al. |
| 2012/0121745 A1 | 5/2012 | Rackl et al. |
| 2013/0121978 A1 | 5/2013 | Asolkar et al. |
| 2013/0196013 A1 | 8/2013 | Asolkar et al. |

FOREIGN PATENT DOCUMENTS

| GB | 1409321 A | 10/1975 |
| KR | 10-0130075 | 4/1998 |
| WO | WO 91/00012 | 1/1991 |
| WO | WO 93/00816 | 1/1993 |
| WO | WO 94/08904 | 4/1994 |
| WO | WO 2007/031565 | 3/2007 |
| WO | WO 2008/012756 | 1/2008 |
| WO | WO 2008/965451 | 6/2008 |
| WO | WO 2008/130558 | 10/2008 |
| WO | WO 2013/130680 | 9/2013 |

OTHER PUBLICATIONS

Molloy et al. Overview of a Novel Green Technology: Biological Control of Zebra and Quagga Missels With *Pseudomonas fluorescens*; (Aug. 24, 2007) downloaded from http://aquaticnuisance.org/wordpress/wp-content/uploads/2009/01/Dreissena-Noyel-Green-Technology-for-Dreissena-Control-4-Malloy.pdf on Feb. 10, 2014.*
Abouseoud, M., "Biosurfactant Production from Olive Oil from *Pseudomonas fluorescens*," *Communicating Current Research and Educational Topics and Trends in Applied Microbiology* p. 340-347 (2007).
Abouseoud, M. et al., "Evaluation of Different Carbon and Nitrogen Sources in Production of Biosurfactant by *Pseeudomonas fluorescens*," *Desalination* 223:143-151 (2008).
Aguedo, M. et al., "Mechanisms Underlying the Toxicity of Lactone Aroma Compounds Towards the Producing Yeast Cells," *Journal of Applied Microbiology* 94:258-265 (2003).
Andersson, R.E. et al., "Lipase Production, Lipolysis, and Formation of Volatile Compounds by *Pseudomonas fluorescens* in Fat Containing Media," *Journal of Food Science* 45:1694-1701 (1980).
Ayer, W.A. et al., "Unsaturated Fatty Acid Lactones from the Fungus *Ophiostoma piliferum*," *Heterocycles* 39:561-569 (1994).
Bangera, G.M. et al., "Identification and Characterization of a Gene Cluster for Synthesis of the Polyketide Antibiotic 2,4-Diacetylphioroglucinol from *Pseudomonas fluorescens* Q2-87," *Journal of Bacteriology* 181(10):3155-3163 (1999).
Barrasa, J.L.M. et al., "Antibacterial Susceptibility Patterns of *Pseudonomas Strains* Isolated from Chronic Canine Otitis Externa," *Journal of Vetirenary Medicine* B 47: 191-196 (2000).
Baum, M.M. et al., "Characterization of Structures in Biofilms Formed by a *Pseudomonas fluorescens* Isolated From Soil," *BMC Microbiology* 9:103 (2009).
Bernabeu, M.C. et al., "(2E,4E)-5-Tosyl-2,4-Pentadienamides: New Dienic Sulfones for the Stereoselective Synthesis of (2E,4E)-Dienamides," *Tetrahedron Letters* 36:3901-3904 (1995).
Blumer, C. et al., "Global GacA-Steered Control of Cyanide and Exoprotease Production in *Pseudomonas fluorescens* Involves Specific Ribosome Binding Sites," *PNAS* 96(24):14073-14078 (1999).
Brader, G. et al. "Alterina Substrate Chain Length Specificity of an Acylhomoserine Lactone Synthase in Bacterial Communication," *J. Biol. Chem.* 280:10403-10409 (2005).
Burgess, J.G. et al., "The Development of a Marine Natural Product-Based Antifouling Paint," *Biofouling* 19(Supplement):197-205 (2003).
Chalier, P. et al., "Enantiodifferentiation of Four y-Lactones Produced by *Penicillium roqueforti*," *Chirality* 10:786-790 (1998).
Chapalain, A. et al., "Comparative Study of 7 Fluorescent Pseudomonad Clinical Isolates," *Canadian Journal of Microbiology* 54:19-27 (2008).
Choi, H.J. et al., "Involvement of Epidermal Growth Factor Receptor-Linked Signaling Responses in *Pseudomonas fluorescens*-Infected Alveolar Epithelial Cells," *Infection and Immunity* 79(5):1998-2005 (2011).
Darrigan, G. et al., "The Golden Mussel, Limnoperna Fortunei (Dunker, 1857) (Bivalvia: Mytilidae), in the Neotropical Region: A 10 Year Story of Invasion," Tentacle No. 11:8-9 (2003).
Deng, W. et al., "Effects of Six-Carbon Aldehydes and Alcohols on Bacterial Proliferation," *Journal of Agricultural and Food Chemistry* 41:506-510 (1993).

(Continued)

*Primary Examiner* — Susan Hanley
*Assistant Examiner* — Paul Martin
(74) *Attorney, Agent, or Firm* — Yuko Soneoka

(57) ABSTRACT

Provided herein are proteins derived from *Pseudomonas* sp., particularly *Pseudomonas protegens*, compositions comprising said proteins and their use in controlling molluscidal activity.

6 Claims, 6 Drawing Sheets

(56) References Cited

OTHER PUBLICATIONS

Dietz, T.H. et al., "Osmotic and Ionic Regulation of North American Zebra Mussels (*Dreissena polymorpha*)," *American Zoologist* 36:364-372 (1996).

Domenech, C.E. et al., "*Pseudomonas aeruginosa* Cholinesterase and Phosphorylcholine Phosphatase: Two Enzymes Contributing to Corneal Infection," *FEMS Microbiology Letters* 82:131-136(1991).

El-Sayed, K.A. et al., "Characterization of the Mupirocin Biosynthesis Gene Cluster from *Pseudomonas fluroescens* NCIMB 10586," *Chemistry & Biology* 10:419-430 (2003).

Flodgaard, L.R. et al., "Nonbioluminescent Strains of *Photobacterium phosphoreum* Produce the Cell-to-Cell Communication Signal N-(3-Hydroxyoctanoyl)homoserine Lactone," *Applied and Environmental Microbiology* 71:2113-2120 (2005).

Furukawa, H. et al., "Ferulic Acid Production from Clove Oil by *Pseudomonas fluorescens* E188," *Journal of Bioscience and Bioengineering* 96(4):404-405 (2003).

Gershman, M.D. et al., "Multistate Outbreak of *Pseudomonas fluorescens* Bloodstream Infection after Exposure to Contaminated Heparinized Saline Flush Prepared by a Compounding Pharmacy," *Clinical Infectious Diseases* 47:1372-1379 (2008).

Gibb, A.P. et al., "Rate of Growth of *Pseudomonas fluorescens* in Donated Blood," *Journal of Clincal Pharmacology* 48:717-718 (1995).

Gimmestad, M. et al., "The *Pseudomonas fluorescens* AlgG Protein, but Not Its Mannuronan C-5-Epimerase Activity, Is Needed for Alginate Polymer Formation," *Journal of Bacteriology* 185(12):3515-3523 (2003).

Guthrie, G.D, et al., "A Bacterial High-Affinity GABA Binding Protein: Isolation and Characterization," *Biochemical and Biophysical Research Communications* 268:65-68 (2000).

Hinsa, S.M. et al., "Biofilm Formation by *Pseudornonas fluorescens* WCS365: A Role for LapD," *Microbiology* 152:1375-1383 (2006).

Hirvonen, M.R. et al., "Bacterial Strains from Moldy Buildings are Highly Potent Inducers of Inflammatory and Cytotoxic Effects," *Indoor Air* 15(Suppl 9):65-70 (2005).

Howell, C.R. et al., "Suppression of Pythium ultimum-Induced Damping-Off of Cotton Seedlings by *Pseudomonas fluorescens* and its Antibiotic, Pyoluteorin," *Phytopathology* 70(8):712-715 (1980).

Hsueh, P. et al., "Outbreak of *Pseudomonas fluorescens* Bacteremia Among Oncology Patients," *Journal of Clinical Microbiology* 36:(10):2914-2917 (1998).

Huttunen, K. et al., "Production of Proinflammatory Mediators by Indoor Air Bacteria and Fungal Spores in Mouse and Human Cell Lines," *Environmental Health Perspectives* 111(1):85-92 (2003).

Ishihara, K. et al., "Effective Production of *Pseudomonas fluorescens* Lipase by Semi-Batch Culture with Turbidity-Dependent Automatic Feeding of Both Olive Oil and Iron Ion," *Applied Microbiology and Biotechnology* 31:45-48 (1989).

Itoh, Y. et al., "A Novel Hepatoprotective γ-Lactone, MH-031. I. Disclovery, Isolation, Physico-Chemical Properties and Structural Elucidation," *J. Antibiotics* 44:832-837 (1991).

Jackson, M.K. et al., "Necrotizing Hepatitis in Pet Birds Associated with *Pseudomonas fiuorescens*," *Avian Diseases* 40:473-476 (1996).

Jiang, Y. et al., "High Poly(β-hydroxybutyrate) Production by *Pseudomonas fluorescens* A2a5 from Inexpensive Substrates," *Enzyme and Microbial Technology* 42:167-172 (2008).

Kanemoto, M. et al,. "Chlorine-Containing Iridoid and Iridoid Glucoside, and Other Glucosides from Leaves of *Myoporum bontioides*," *Phytochemistry* 69:2517-2522 (2008).

Karatayev, A.Y. et al., "The Effects of *Dreissena polymorpha* (Pallas) Invasion on Aquatic Communities in Eastern Europe," *J. Shellfish Research* 16:187-203 (1997).

Kisaalita, W.S. et al., "Defined Media for Optimal Pyoverdine Production by *Pseudomonas fluorescens* 2-79," *Applied Microbiology and Biotechnology* 39:750-755 (1993).

Kiuchi, F. et al., "Studies on Crude Drugs Effective on Visceral Larva Migrans. IV. Isolation and Identification of Larvicidal Principles in Pepper," *Chem. Pharm. Bull.* 36:2452-2465 (1998).

Kojima, Y. et al., "Purification and Characterization of an Alkaline Lipase from *Pseudomonas fluorescens* AK102," *Biosci. Biotech. Biochem.* 58(9):1564-1568 (1994).

Koka, R. et al., "Isolation and Characterization of a Protease from *Pseudomonas fluorescens* R098," *Journal of Applied Microbiology* 89:280-288 (2000).

Kramer, K.J.M. et al., "The Musselmonitor®' as Biological Early Warning System, The First Decade," in *Biomonitors and Biomarkers as Indicators of Environmental Change 2, Environmental Science Research* 56:59-87 (2000).

Li, C.-Y. et al., "Isolation and Identification of Antiplatelet Aggregatory Principles from the Leaves of Piper Lolot," *J. Agric. Food Chem.* 55:9436-9442 (2007).

Likhitwitayawuid, K. et al., "Structural Elucidation and Synthesis of New Components Isolated from *Piper sarmentosum* (Piperaceae)," *Tetrahedron* 43:3689-3694 (1987).

Liao, C. et al., "Biochemical and Genetic Characterization of an Extracellular Protease from *Pseudomonas fluorescens* CY091," *Applied and Environmental Microbiology* 64(3):914-921 (1998).

Lorenzo, M. et al., "$^{13}$C NMR-Based Empirical Rules to Determine the Configuration of Fatty Acid Butanolids. Novel y-Dilactones from *Pterogorgia* spp," *Organic Letters* 8:5001-5004 (2006).

Ma, C. et al., "Anti-Tuberculosis Constituents from the Stem Bark of *Micromelum hirsutum*," *Planta Med.* 71:261-267 (2005).

Macisaac, H.J., "Potential Abiotic and Biotic Impacts of Zebra Mussels on the Inland Waters of North America," *Amer. Zool.* 36:287-299 (1996).

Mackie, G.L. et al., "Comparative Biology of Zebra Mussels in Europe and North America: An Overview," *American Zoologist* 36:244-258 (1996).

Madi, A. et al., "The Clinical *Pseudomonas fluorescens* MFN1032 Strain Exerts a Cytotoxic Effect on Epithelial Intestinal Cells and Induces Interleukin-8 via the AP-1 Signaling Pathway," *BMC Microbiology* 10:215 (2010).

Madi, A. et al., "*Pseudomonas fluorescens* Alters Epithelial Permeability and Transiocates Across Caco-2/TC7 Intestinal Cells," *Gut Pathogens* 2:16 (2010).

Manfredi, R. et al., "*Pseudomonas* Organisms Other than *Pseudomonas aeruginosa* as Emerging Bacterial Pathogens in Patients with Human Immunodeficiency Virus Infection," *Infectious Diseases in Clinical Practice* 9:79-87 (2000).

McMahon, R.F., "The Physiological Ecology of the Zebra Mussel, *Dreissena polymorpha*, in North America and Europe," *American Zoologist* 36:339-363 (1996).

Miller, S.L. et al., "Axinellamide, a New Alkaloid from the Marine Sponge *Axinella* Sp.," *Tetrahedron Letters* 36:5851-5852 (1995).

Mills, E.L. et al., "A Review of the Biology and Ecology of Quagga Mussel (*Dreissena bugensis*), a Second Species of Freshwater Dreissenid Introduced to North America," *American Zoologist* 36:271-286 (1996).

Mizobuchi, S. et al., "Antifouling Substances Against the Mussel in an Octocoral *Dendronephthya* sp.," *Nippon Suisan Gakkaishi* 59(7):1195-1199 (1993).

Molloy, D.P., "The Potential for Using Biological Control Technologies in the Management of *Dreissena* Spp.," *J. Shellfish Res.* 17:177-183 (1998).

Molloy, D.P. et al., "Overview of a Novel Green Technology: Biological Control of Zebra and Quagga Mussels with *Pseudomonas fluorescens*," *Bacterial Project Overview* 6:1-9 (2207).

Molloy, D.P., "Environmentally Safe Control of Zebra Mussel Fouling," Technical Report (R41909R09) retrieved from the internet at http://www.netl.doe.gov/technologies/coalpower/ewr/pubs/ NT41909_NY%20Dept%20of%20Educ_Final%20Report.pdf (May 21, 2008).

Molloy, D.P. et al., "Mode of Action of *Pseudomas fluorescens* Strain CL145A, a Lethal Control Agent of Dreissenid Mussels (Bivalvia: Dreissenidae)," *J. Invertebrate Pathology* 113:115-121 (2013).

Murty, M.G. et al., "Production of a Mosquitocidal Exotoxin by a *Pseudomonas fluorescens* Strain," *Journal of invertebrate Pathology* 64:68-70 (1994).

(56) References Cited

OTHER PUBLICATIONS

Nakamura, S. et al., "Green-Leaf-Derived C6-Aroma Compounds with Potent Antibacterial Action That Act on Both Gram-Negative and Gram-Positive Bacteria," *Journal of Agricultural and Food Chemistry* 50:7639-7644 (2002).
Nowak-Thompson, B. et al., "Characterization of the Pyoluteorin Biosynthetic Gene Cluster of *Pseudomonas fluorescens* Pf-5," *Journal of Bacteriology* 181(7):2166-2174 (1999).
Oliveira, M.D. et al., "Forecasting the Expansion of the Invasive Golden Mussel Limnoperna fortune in Brazilian and North American Rivers Based on its Occurrence in the Paraguay River and Pantanal Wetland of Brazil," *Aquatic Invasions* 5:59-73 (2010).
Østgaard, K., "Enzymatic Microassay for the Determination and Characterization of Alginates," *Carbohydrate Polymers* 19:51-59 (1992).
Parente, A.M. et al., "Ultrastructural Aspects of Autolysis of *Pseudomonas fluorescens* Induced by Osmotic Shock," *Journal of General Microbiology* 130:1459-1470 (1984).
Peighami-Ashnaei, S. et al., "Interaction of Different Media on Production and Biocontrol Efficacy of *Pseudomonas fluorescens* P-35 and *Bacillus subtilis* B-3 Against Grey Mold of Apple," *Journal of Plant Pathology* 91(1):65-70 (2009).
Perry. K. et al., "Detecting Physiological and Pesticide-Induced Apoptosis in Early Developmental Stages of Invasive Bivalves," *Hydrobiologia* 628:153-164 (2009).
Peyer, S.M. et al., "Zebra Mussels Anchor Byssal Threads Faster and Tighter than Quagga Mussels in Flow," *The Journal of Experimental Biology* 212:2027-2036 (2009).
Picot, L. et al., "*Pseudomonas fluorescens* as a Potential Pathogen: Adherence to Nerve Cells," *Microbes and Infection* 3:985-995 (2001).
Prabakaran, G. et al., "Isolation of a *Pseudomonas fluorescens* Metabolite/Exotoxin Active Against Both Larvae and Pupae of Vector Mosquitoes," *Pest Management Science* 59:21-24 (2002).
Prabakaran, G. et al., "Development of Cost-Effective Medium of the Large-Scale Production of a Mosquito Pupicidal Metabolite from *Pseudomonas fluorescens* Migula," *Biological Control* 48:264-266 (2009).
Rajmohan, S. et al., "Enzyme from Isolates of *Pseudomonas fluorescens* Involved in Food Spoilage," *Journal of Applied Microbiology* 93:205-213 (2002).
Ramette, A. et al., "*Pseudomas protegens* sp. nov., Widespread Plant-Protecting Bacteria Producing the Biocontrol Compounds 2,4-Diacetylphloroglucinol and Pyoluteorin," *Systematic and Applied Microbiology* 34:180-188 (2011).
Rezanka, T. et al., "γ-Lactones from the Soft Corals *Sarcophyton trocheliophorum* and *Lithophyton arboreum*," *Tetrahedron* 57:8743-8749 (2001).
Ricciardi, A., "Global Range Expansion of the Asian Mussel *Limnoperna fortunei* (*Mytilidae*): Another Fouling Threat to Freshwater Systems," *Biofuling* 13(2):97-106 (1998).
Ricciardi, A. et al., "Impending Extinctions of North American Freshwater Mussels (*Unionoida*) Following the Zebra Mussel (*Dreissena polymorpha*) Invasion," *J. Animal Ecology* 67:613-619 (1998).
Rochu, D. et al., "Purification, Molecular Characterization and Catalytic Properties of *Pseudomonas fluorescens* Enzyme Having Cholinesterase-Like Activity," *Biochemica et Biophysica Acta* 1385:126-138 (1998).
Rossignol, G. et al., "Involvement of a Phospholipase C in the Hemolytic Activity of a Clinical Strain of *Pseudomonas fluorescens*," *BMC Microbiology* 8:189 (2008).
Rossignol, G. et al., "Phenotypic Variation in the *Pseudomonas fluorescens* Clinical Strain MFN 1032," *Research in Microbiology* 160:337-344 (2009).
Rukachaisirikul, T. et al., "Chemical Constituents of Bioactivity of *Piper sarmentosum*," *J. Ethnopharmacology* 93:173-176 (2004).
Sandler, J.S. et al., "Cytotoxic β-Carbolines and Cyclic Peroxides from the Palauan Sponge *Plakortis nigra*," *J. Nat. Prod.* 65:1258-1261 (2002).
Seo, S-T et al., "Characterization of an Antibacterial Substance Produced by *Erwinia carotovora* subsp. carotovora Ecc 32," *J. Gen. Plant Pathol.* 70:273-277 (2004).
Shaaban, K.A. et al., "Electrospray Ionization Mass Spectra of Piperazirnycins A and B and y-Butyrolactones from a Marine-Derived *Streptomyces* sp.," *J. Antibiot.* 61:736-746 (2008).
Shen, Y-C. et al., "Novel Linear $C_{22}$-Sesterterpenoids from *Sponge Ircinia formosana*," *Tetrahedron Letters* 47:4007-4010 (2006).
Shimizu, I. et al., "The Antibacterial Activity of Fragrance Ingredients Against *Legionella pneurnophila*," *Biol. Pharm. Bull.* 32:1114-1117 (2009).
Silby, M.W, et al., "*Pseudomonas* Genomes: Diverse and Adaptable," *FEMS Microbiology Reviews* 35:652-680 (2011).
Silverman, H. et al., "Gill Structure in Zebra Mussels: Bacterial-Sized Particle Filtration," *American Zoologist* 36:373-384 (1996).
Sugiura, M. et al., "Purification, Crystallization and Properties of Triacylglycerol Lipase from *Pseudomonas fluorescens*," *Biochimica et Biophysica Acta* 488:353-358 (1977).
Sutherland, R. et al., "Antibacterial Activity of Mupirocin (Pseudomonic Acid), A New Antibiotic for Topical Use.," *Antimicrobial Agents and Chemotherapy* 27(4095-498 (1985).
Takougang, I. et al., "Field Trials of Low Dose Bayluscide on Snail Hosts of Schistosome and Selected Non-Target Organisms in Sahelian Cameroon," *Mem. Inst. Oswaldo Cruz* 101(4):355-358 (2006).
Tan. K.H. et al., "Effect of Culture Conditions on Batch Growth of *Pseudomonas fluorescens* on Olive Oil," *Applied Microbiology and Biotechnology* 23:27-32 (1985).
Tan, K.H. et al., "Utilization of Substrates During Batch Growth of *Pseudomonas fluorescens* on Olive Oil, Lard, and Mutton Tallow," *Applied Microbiology and Biotechnology* 26:443-446 (1987).
Thomashow, L.S. et al,, "Role of a Phenazine Antibiotic from *Pseudomonas fluorescens* in Biological Control of *Gaeumannomyces graminis* var. *tritici*," *Journal of Bacteriology* 170(8):3499-3508 (1988).
Tuntiwachwuttikul, P. et al., "Chemical Constituents of the Roots of *Piper Sarmentosum*," *Chem. Pharm. Bull.* 54:149-151 (2006).
U.S. Army Corps of Engineers Waterways Experiment Station, "Zebra Mussels: Biology, Ecology, and Recommended Control Strategies," Zebra Mussel Research Technical Note ZMR-1-01, Zebra Mussel Research Program, 9 pages (1995).
U.S. Geological Survey, Florida Caribbean Science Center, "Nonindigenous Species Information Bulletin: Asian Clam, *Corbicula fluminea*," No. 2001-001 (2001).
Veron, W. et al., "Natriuretic Peptides Modify *Pseudomonas fluorescens* Cytotoxicity by Regulating Cyclic Nucleotides and Modifying LPS Structure," *BMC Microbiology* 8:114 (2008).
Vieira, P.C. et al., "γ-Lactones from *Iryanthera* Species," *Phytochemistry* 22:711-713 (1983).
Von Graevenitz, A. et al., "Pathogenic Significance of *Pseudomonas fluorescens* and *Pseudornonas putida*," *Yale Journal of Biology and Medicine* 44:265-273 (1971).
Wagner, S.J. et al., "Transfusion-Associated Bacterial Sepsis.," *Clinical Microbiology Reviews* 7(3):290-302 (1994).
Wang, S. et al., "Production of Antifungal Materials by Bioconversion of Shellfish Chitin Wastes Fermented by *Pseudomonas fluorescens* K-188," *Enzyme and Microbial Technology* 36:49-56 (2005).
Wei, B. et al., "*Pseudornonas fluorescens* Encodes the Crohn's Disease-Associated I2 Sequence and T-Cell Superantigen," *Infection and Immunity* 70(12):6567-6575 (2002).
Williams, P.G. et al., "Arenicolids A-C, 26-Membered Ring Macrolides from the Marine Actinomycete *Salinispora arenicola*," J. Org. Chem. 72:502505034 (2007).
Winson, M.K. et al., "Multiple N-acyl-L-Homoserine Lactone Signal Molecules Regulate Production of Virulence Determinants and Secondary Metabolites in *Pseudomonas aeruginosa*," *PNAS* 92:9427-9431 (1995).

\* cited by examiner

USE OF PROTEINS ISOLATED FROM *PSEUDOMONAS* TO CONTROL MOLLUSCS

TECHNICAL FIELD

Provided herein are proteins derived from *Pseudomonas* sp., particularly *Pseudomonas protegens*. These proteins in a particular embodiment have molluscicidal activity.

BACKGROUND

The ability of the mussels to quickly colonize new areas, rapidly achieve high densities and attach to any hard substratum (e.g., rocks, logs, aquatic plants, shells of native mussels, exoskeletons of crayfish, plastic, concrete, wood, fiberglass, pipes made of iron and polyvinyl chloride and surfaces covered with conventional paints) make it possible for them to cause serious adverse consequences. These consequences include damages of water-dependent infrastructure, millions of dollars increase in the operating expense and significant damage to the ecological systems.

Management of mussels is very important for protecting water-dependent infrastructure and aquatic ecological systems. There are many proactive and reactive methods to control and reduce the populations of mussels. Reactive removal includes the mechanical removal, predator removal, and chemical and biochemical removal of adult mussels. For example, fish, birds, crayfish, crabs, leeches and mammals have shown to predate mussels. However, it is unlikely that invasive mussel populations will be controlled by natural predation, especially in man-made structures such as pipes or pumping plants. Proactive measures to control mussels includes any mechanical, physical or chemical means in witch the planktonic (veliger) mussel life stage is prevented from settling and growing into the adult life stage or colonizing on hard substrates. Preventing mussels from colonizing and growing into adult life stages is also referred to as settlement prevention.

Molluscicides

Exploitation of environmentally friendly biopesticides for effective control of invasive mussels is crucial to avoid water resources from damage of harmful chemicals. To reach such a goal, more than 700 bacterial isolates were screened as potential biological control agents to be used against zebra and quagga mussels from New York State Museum's (NYSM) Field Research Laboratory. One of these strains, *Pseudomonas fluorescens* (CL 145A), was found to be lethal to these mussels (see Molloy, D. P. U.S. Pat. No. 6,194,194, issued Feb. 27, 2001). This bacterium is worldwide in distribution and is present in all North American waterbodies. In nature it is a harmless bacterial species and found to protect the roots of plants from rot and mildew. It is so ubiquitous that it is a common food spoilage organism in the average household refrigerator [Daniel P. Molloy and Denise A. Mayer, Overview of a Novel Green Technology Biological Control of Zebra and Quagga Mussels with *Pseudomonas fluorescens*, Version 6: Updated Aug. 24, 2007]. This strain has also been found to be active against golden mussels (see PCT appln. pub. No. WO2012/065038) and various fungi and bacteria (see PCT appln. no. PCT/US2013/028112). Lactones and fatty acids were found as active ingredients (US Patent Appln Pub. No. US20100266717A1). However, quantity and mussel toxicity of such active ingredients could not explain of the mussel toxicity of the whole bacterium.

Fumarate Hydratase

Fumarate hydratase, an enzyme, is also called fumarase, L-malate hydrolyase or (S)-malate hydrolyase. Its main function is to catalyze the reversible hydration/dehydration of fumarate to malate. This enzyme is in mitochondrial and cytosolic. The mitochondrial isoenzyme is involved in the Krebs Cycle (also known as the Tricarboxylic Acid Cycle [TCA] or the Citric Acid Cycle), and the cytosolic isoenzyme is involved in the metabolism of amino acids and fumarate. In the citric acid cycle, it facilitates a transition step in the production of energy in the form of NADH. In the cytosol, it metabolizes fumarate, which ends up as a byproduct of the urea cycle as well as amino acid catabolism. In plants, it functions as reductive citric acid cycle ($CO_2$ fixation), and in mammals it is involved in renal cell carcinoma.

Depending on the arrangement of their relative subunit, their metal requirement, and their thermal stability, fumarases can be classified into two classes (I & II). Class I fumarases are able to change state or become inactive when subjected to heat or radiation, are sensitive to superoxide anion, are Iron II ($Fe^{2+}$) dependent, and are dimeric proteins consisting of around 120 kD. Class II fumarases, found in prokaryotes as well as in eukaryotes, are tetrameric enzymes of 200,000 D that contain three distinct segments of significantly homologous amino acids. They are also iron-independent and thermal-stable. Prokaryotes are known to have three different forms of fumarase: fumarase A, fumarase B, and fumarase C. fumarase C is a part of the class II fumarases, whereas fumarase A and fumarase B from *Escherichia coli* (*E. coli*) are classified as class [Estévez M, Skarda J, Spencer J, Banaszak L, Weaver TM (June 2002). "X-ray crystallographic and kinetic correlation of a clinically observed human fumarase mutation". Protein Sci. 11(6): 1552-7].

Fumarases have been found to play a role in a number of metabolic disorders. For example, benign mesenchymal tumors of the uterus, leiomyomatosis and renal cell carcinoma, and fumarase deficiency are related to fumarase mutation and development. It is also related to fetal brain abnormalities [reviewed in Deschauer M, Gizatullina Z, Schulze A, Pritsch M, Knoppel C, Knape M, Zierz S, Gellerich F N. Molecular and biochemical investigations in fumarase deficiency. Mol Genet Metab. 2006 June; 88(2):146-52. Epub 2006 Feb. 28.] Except for these functions, whether there is an additional function, especially in mussel, is unknown.

Dihydrolipoamide Dehydrogenase

Dihydrolipoamide dehydrogenase, a mitochondrial enzyme, is also called dihydrolipoyl dehydrogenase. It degrades dihydrolipoamide and produces lipoamide. It is a part (a subunit) of several enzyme complexes (groups of enzymes that work together). These complexes are essential for the breakdown of certain molecules to produce energy in cells. Dihydrolipoamide dehydrogenase forms a subunit called the E3 component that is shared by several enzyme complexes including pyruvate dehydrogenase complex, 2-oxo-glutarate complex, branched chain keto acid dehydrogenase complex. Deficiency of E3 component will be involved in human diseases such as maple syrup urine disease [Shaag A et al. (1999). "Molecular basis of lipoamide dehydrogenase deficiency in Ashkenazi Jews." *Am. J. Med. Genet.* 82(2):177-82.]. Except for these functions, whether there is an additional function, especially in mussel, is unknown.

SUMMARY

Provided are proteins and isolated cell fractions derived from *Pseudomnas* sp. comprising said proteins for use in controlling molluscs, particularly members of the Gastropoda and/or Bivalvia classes and more particularly mussels, snails and slugs and even more particularly, *Dreissana* species and yet even more particularly, zebra or quagga mussels.

In a particular embodiment, the proteins are enzymes; in a more particular embodiment, the enzyme has fumarate hydratase activity or has dihydrolipoamide dehydrogenase activity. In an even more particular embodiment, the enzyme having fumarate hydratase activity has about 80% homology to SEQ ID NO:6 and may be encoded by the nucleic acid sequence having 80% homology to SEQ ID NO:7. Alternatively, the enzyme having dihydrolipoamide dehydrogenase activity has about 80% homology to SEQ ID NO:8 and may be encoded by the nucleic acid sequence having about 80% homology to SEQ ID NO:9. Also provided are the nucleic acid molecules encoding an enzyme having fumarate hydrate or an enzyme having dihydrolipoamide dehydrogenase activity. In a particular embodiment, the nucleic acid molecule has about 80% homology to SEQ ID NO:8; in another embodiment, the nucleic acid molecule has about 80% homology to SEQ ID NO:9.

Therefore provided is a method for controlling one or more molluscs in a location where control is desired comprising introducing into said location at least one of these proteins and/or a cell fraction derived from *Pseudomans* sp. comprising at least one of these proteins comprising in particular, an enzyme having fumarate hydratase activity and/or dihyrolipoamide dehydrogenase activity in amounts effective to control said molluscs.

In a related aspect, provided is a molluscidal composition comprising at least one of said (a) an enzyme having fumarate hydratase activity and/or an enzyme having dihyrolipoamide dehydrogenase activity or cell fraction comprising the enzymes set forth above and (b) a surfactant and/or molluscicidal carrier and optionally (c) a second molluscicidal substance and a method for controlling one or more molluscs in a location where control is desired using said compositions.

Also provided are methods for obtaining these proteins. In a particular embodiment, the method comprises:
(a) providing a *Pseudomonas* strain and
(b) isolating the protein from said *Pseudomonas* strain.

In a particular embodiment, the *Pseudomonas* strain has one or more identifying characteristics of *Pseudomonas protegens* or *Pseudomonas fluorescens* and more particularly *Pseudomonas* strain ATTC 55799.

In another particular embodiment, the method for isolating the protein comprises applying cells from said Psuedomonas strain to a column (e.g., ion exchange column) and isolating the protein having either fumarate hydratase activity or dihyrolipoamide activity from fractions of said column.

The protein may also be obtained by
(a) culturing a transformed cell comprising a nucleic acid molecule encoding an enzyme having fumarate hydratase activity or dihyrolipoamide dehydrogenase activity for a time sufficient to express said enzyme and
(b) isolating said enzyme expressed in (a) having fumarate hydratase activity or dihyrolipoamide dehydrogenase activity.

DETAILED DESCRIPTION

Figure 1:
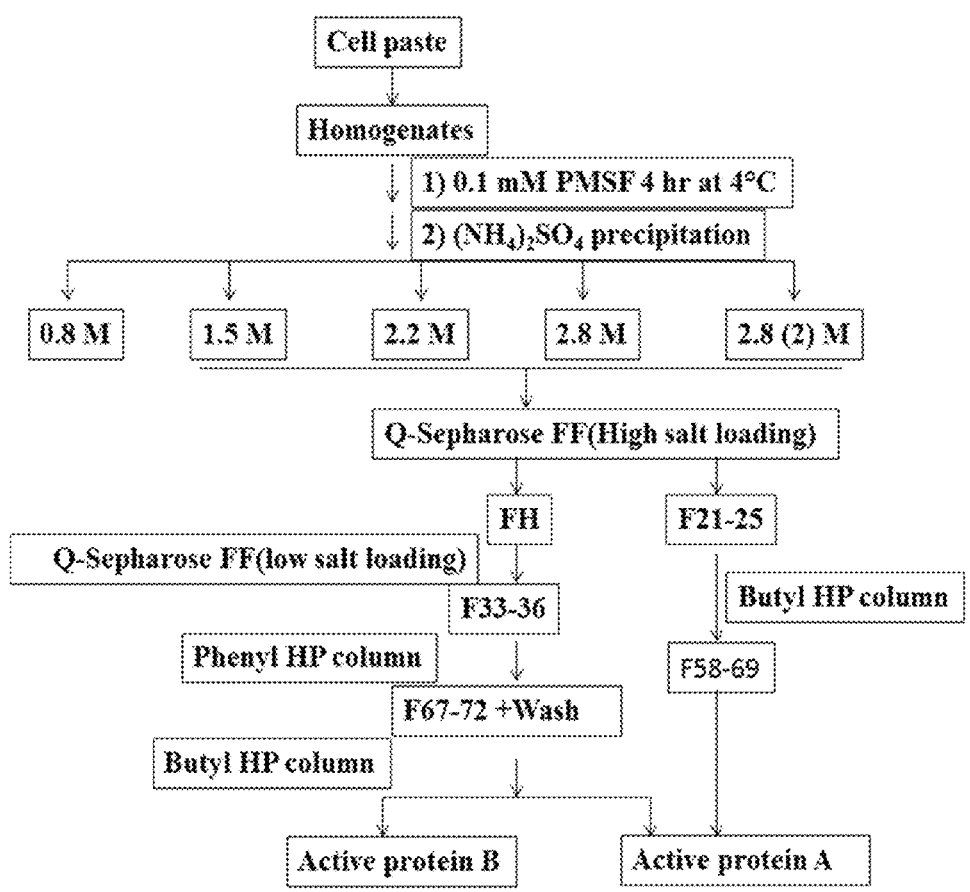
FIG. 1 shows the scheme used to obtain proteins.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "controlling molluscs" means controlling the eggs, larvae, veligers and post-veligers of the molluscs by killing or disabling them so that they cannot colonize, grow, establish, or reproduce in a given location.

As defined herein, "derived from" and "obtainable from" means directly isolated or obtained from a particular source or alternatively having identifying characteristics of a substance or organism isolated or obtained from a particular source. These terms are used interchangeably throughout the specification.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods.

As defined herein, a "nucleic acid molecule", is intended to include DNA molecules and RNA molecules. A nucleic acid molecule may be single-stranded or double-stranded, but preferably is double-stranded DNA.

As defined herein, a "vector", is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As defined herein, the terms "recombinant host cell" and "transformed host cell" are used interchangeably and refer to a cell into which a recombinant expression vector and/or an isolated nucleic acid molecule has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein.

The following terms are used to describe the sequence relationships between a polynucleotide/polypeptide of the present invention with a reference polynucleotide/polypeptide: (a) "reference sequence", (b) "comparison window", (c) "sequence identity", and (d) "percentage of sequence identity".

As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet et al., Nucleic Acids Research 16:10881-90 (1988); Huang et al., Computer Applications in the Biosciences 8:155-65 (1992), and Pearson et al., Methods in Molecular Biology 24:307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See Current Protocols in Molecular Biology, Chapter 19, Ausubel et al., Eds., Greene Publishing and Wiley-Interscience, New York (1995); Altschul et al., J. Mol. Biol., 215:403-410 (1990); and, Altschul et al., Nucleic Acids Res. 25:3389-3402 (1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see e.g., Karlin & Altschul, Proc. Nat'l. Acad. Sci. USA 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149-163 (1993)) and XNU (Clayerie and States, Comput. Chem., 17:191-201 (1993)) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (J. Mol. Biol. 48:443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89:10915).

Multiple alignment of the sequences can be performed using the CLUSTAL method of alignment (Higgins and Sharp (1989) CABIOS. 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Enzymes

The enzymes used in the methods for controlling molluscs may have fumarate hydratase activity or has dihydrolipoamide dehydrogenase activity. In an even more particular embodiment, the enzyme having fumarate hydratase activity has about 80%, 85%, 90%, 95%, 97%, 99%, 99.5%, 99.9% homology or sequence identity to SEQ ID NO:6. Alternatively, the enzyme having dihydrolipoamide dehydrogenase activity has about 80%, 85%, 90%, 95%, 97%, 99%, 99.5%, 99.9% homology or sequence identity to SEQ ID NO:8.

The enzymes may be obtained, or are obtainable or derived from an organism having the identifying characteristics of a *Pseudomonas* species, more particularly, from an organism having the identifying characteristics of a strain of *Pseudomonas fluorescens* or alternatively from an organism having the identifying characteristics of *Pseudomonas fluorescens* isolate, ATCC 55799 as set forth in U.S. Pat. No. 6,194,194. The methods comprise cultivating these organisms and optionally obtaining the compounds by isolating these compounds from the cells of these organisms.

In particular, the organisms are cultivated in a nutrient medium using methods known in the art, which may include but is not cultivation by shake flask cultivation, small scale or large scale fermentation (including but not limited to continuous, batch, fed-batch, or solid state fermentations) in laboratory or industrial fermentors performed in suitable medium and under conditions allowing cell growth. The cultivation may take place in suitable nutrient medium comprising carbon and nitrogen sources and inorganic salts, using procedures known in the art. Suitable media are available may be available from commercial sources or prepared according to published compositions. A particular embodiment is disclosed in the examples infra and in U.S. Pat. No. 6,194,194.

After cultivation, the cells may be concentrated and subsequently suspended in a buffer to obtain a cell suspension. In one embodiment, a suspension of dead cells is used. Live cells in the cellular suspension may be killed by at least one of the following: irradiating, heating, drying, r treating cells with other chemical of physical means. A dead cell suspension is not required for activity against mussel species.

In a particular embodiment, substances toxic to molluscs may be extracted from the suspension. The extract may be fractionated by chromatography. Chromatographic fractions may be assayed for toxic activity against molluscs, such as mussels, snails (e.g., aquatic and/or garden snails) and/or slugs, using methods known in the art; one particular embodiment is disclosed in the examples, infra. This process may be repeated one or more times using the same or different chromatographic methods. They will also be assayed for dihydrolipoamide dehydrogenase and/or fumarat hydratase activity.

Nucleic Acid Molecules

Also provided are nucleic acid molecules that encode said enzymes. These nucleic acid molecules possess at least about 80%, 85%, 90%, 95%, 97%, 99%, 99.5%, 99.9% sequence identity to SEQ ID NO:7 or SEQ ID NO:9. These nucleic acid molecules may be DNA, RNA, cDNA, cRNA or analog sequences. They may be obtained from a *Pseudomonas* strain or by chemical synthesis or by recombinant methods known in the art. Specifically nucleic acid libraries may be constructed, screened and amplified. For example, a cDNA or genomic library can be screened using a probe based upon the sequence of a polynucleotide disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

These nucleic acid molecules may be inserted into vectors. The vectors may be expression vectors. Recombinant expression vectors containing a sequence encoding these nucleic acid molecules are thus provided. The expression vector may contain one or more additional polynucleotide sequences, such as but not limited to regulatory sequences, a selection marker, a purification tag, or a polyadenylation signal. Such regulatory elements may include a transcriptional promoter, enhancers, mRNA ribosomal binding sites, or sequences that control the termination of transcription and translation.

Expression vectors, especially mammalian expression vectors, may include one or more nontranscribed elements, such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, recombination sites, or transcriptional termination sequences. An origin of replication that confers the ability to replicate in a specific host may also be incorporated.

The vectors may be used to transform any of a wide array of host cells known to those of skill in the art. Vectors include without limitation, plasmids, phagemids, cosmids, bacmids, bacterial artificial chromosomes (BACs), yeast artificial chromosomes (YACs), and baculovirus vectors, as well as other bacterial, eukaryotic, yeast, and viral vectors.

Formulations

The enzymes and cell fractions comprising said enzymes set forth above may be useful in controlling molluscs, particularly members of the Gastropoda and/or Bivalvia classes and more particularly mussels, snails and slugs. The enzymes can be made into compositions (also alternatively referred to as "formulations") and can be formulated in any form. Non-limiting formulation examples include emulsifiable concentrates (EC), wettable powders (WP), soluble liquids (SL), aerosols, ultra-low volume concentrate solutions (ULV), soluble powders (SP), microencapsulation, water dispersed granules, flowables (FL), microemulsions (ME), nano-emulsions (NE), etc. In any formulation described herein, percent of active ingredient is within a range of 0.01% to 99.99%. In a particular embodiment, the formulations may be free of surfactants. Alternatively, the formulations may contain surfactants including but not limited to In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactants may range between 0.1-35% of the total formulation, preferred range is 5-25%.

The enzymes or cell fractions may be formulated with other molluscicidal substances which Examples include but are not limited to chlorine and substances disclosed in US20100266717A1 and includes but is not limited to a lactone, lactam, carbamate, carboxylic acid and amide and said compounds are members of a family of compounds selected from the group consisting of:

(a) family I, wherein a family I compound possesses following chemical structure:

$$\underset{A\diagdown\underset{n}{M}}{\overset{\overset{Y}{\|}}{X}}(R)z$$

Wherein X is carbon; Y is oxygen; A and M are carbon, oxygen, nitrogen, sulfur and n is 1 to 21

Wherein $(R)_z$ represents number Z of the number of substituents on the group R on the ring wherein R and the substituents on R are selected from the group consisting of hydrogen, hydroxyl, alkyl hydroxyl, alkenyl hydroxyl, alkynyl hydroxyl, alkyloxy, alkenyloxyl, alkynylxoy, cycloalkyl, cycloalkenyl, alkyl, alkenyl, alkynyl, heterocyclyl, heteroaryl, aromatic, aryl group, NH-substituted, and N,N-substituted group; the length of the R chain is from 1 to 25 atoms, and Z is 0, 1, 2, 3;

(b) family II, wherein a family II compound possesses the following chemical structure:

$$\underset{[\underset{n}{\diagup}B}{\overset{\overset{Y}{\|}}{X}}(R)z$$

Wherein X is carbon; Y is oxygen; A, B and M are carbon, oxygen, nitrogen and sulfur; Wherein (R)z represents number Z of the number of substituents on the group R on the ring; R and the substituents on R is selected from the group consisting of a hydrogen, hydroxyl, alkyl hydroxyl, akenyl hydroxyl, alkynyl hydroxyl, alkyloxy, alkenyloxyl, alkynylxoy, alkyl, alkenyl, alkynyl, heterocyclyl, aromatic, aryl group, NH-substituted, and N,N-substituted group; the length of the R chain is from 1 to 25 atoms, and Z is 0, 1, 2, 3;

(c) family III, wherein a family III compound possesses following chemical structure:

Wherein X is carbon; Y is oxygen; Z is hydrogen, hydroxyl, alkenyl hydroxyl, alkynyl hydroxyl, alkyl, alkenyl, alkynyl, heterocyclyl, aromatic, aryl group, NH-substituted, or N,N-substituted group.

Wherein R is alkenyl hydroxyl, alkynyl hydroxyl, alkyl, alkenyl, alkynyl, heterocyclyl, aromatic, aryl group, NH-substituted, or N,N-substituted group 1 to 50 atoms in length.

The cell fractions or enzymes may be formulated with inert materials that include but are not limited to inorganic minerals such as kaolin, mica, gypsum, phyllosilicates, carbonates, sulfates, or phosphates; or botanical materials such as wood products, cork, powdered corn cobs, rice hulls, peanut hulls and walnut shells. In a particular embodiment, the inert material can be obtained or derived from a clay mineral (kaolinite, smectite, attapulgite) suspended in water at a rate of about 1 to 20 mg/liter corresponding to approximately 1 to 20 NTU (normalized turbidity units). The inert materials used to enhance mussel siphoning can be applied in solid form or as a suspension in aqueous solution, preferably water, directly to the water or the location (e.g., solid surface) where the mussels are treated. In a particular embodiment, to enhance product efficacy, an inert material such as clay, silt, sediment or any other material with no nutritional value and with a small enough particle size can be suspended in water prior to the treatment with a chemical or a biopesticide product.

Methods of Use

The compounds and compositions of the present invention may be used to control molluscs, particularly, a member of the Gastropoda and/or Bivalvia class, more particularly mussels (e.g., *Dreissana* species) and/or Gastropoda, particularly, snails, which includes but is not limited to aquatic snails (e.g., *Biomphalaria* species) and garden snails, including but not limited to brown garden snails, white garden snails (e.g., *Cantareus* species, *Cornu* species, Theba species), and/or slugs, including but not limited to gray garden slug (e.g., *Deroceras* sp.), the banded or three-band slug (e.g., *Lehmannia* sp.), the tawny slug (e.g., *Limacus* sp.), and the greenhouse slug (e.g., *Milax* sp.) in a body of water or on surfaces where molluscs such as mussels, snails and/or slugs gather or alternatively as an anti-fouling agent in paint. In the event that it is used as an antifouling agent in paint, it is present in an anti-vegetative, biocidally effective amount. Surfaces where molluscs such as mussels, snails and/or slugs include but are not limited to plastic, concrete, wood, fiberglass, pipes made of iron and polyvinyl chloride and surfaces covered with paints and/or coatings. Coatings may be formulated from pigments, binders, additives, and/or carrier fluids and are preferably applied in a thin film to provide protection or decoration to a surface. The end product (which contains the active compound) will be used at 10-200 mg/L, more specifically at 25-100 mg/L (ppm) or 25-10000 mg/kg. It will be applied either as a dry product or suspended in water into pipes, dam structures, holding tanks, and open waters such as streams, rivers, lakes, irrigation canals, ponds and lakes through specific application pumps and mixing systems.

In a particular embodiment, the present invention is directed to a method for improving biopesticidal and pesticidal activity of materials used to control invasive molluscs, particularly mussels comprising the steps of:

1. suspension of inert material such as clay into the water to trigger the siphoning activity for about 1-24 hours before the chemical or biopesticide treatment
2. addition of a chemical or a biopesticide into the water at a desired level The invention is also directed to a method comprising a step of administering a microbial biopesticide in combination of an inert material such as clay to enhance the uptake and hence, mortality of mussels.

To activate the mussel siphoning, this clay (turbidity) treatment should be carried on for about 1 to 6 hours, usually about 3-4 hours, and for about 1 to 24 hours, typically about 14-18 hours before the treatment with a chemical/pesticide. Alternatively, the turbidity treatment can be applied simultaneously with the chemical or biopesticide treatment.

According to the one embodiment of this invention, treatment of molluscs, such as mussels, snails and slugs can be carried out in 500-mL glass jars or in a biobox constructed of acrylic sheets. In the glass jars, aeration during treatment is provided by airflow through aquarium air stones connected to nylon tubing. In the biobox, water is constantly flowing at a rate of 1 gallon per minute.

The materials for the turbidity treatment as well as for the chemical/biopesticide product can be mixed in the water by pipetting or via a peristaltic pump. In bioboxes, a more uniform mixing is achieved using a paddle mixer at the point of injection. The compositions of the present invention can be in a suitable form for direct application or as a concentrate or primary composition, which requires dilution with a suitable quantity of water or other diluent before application.

The effective amount of the turbidity materials will depend upon the application, water temperature, if applied to water, and duration of the treatment. In general, the composition may be applied at a rate of from about 1 to about 20 mg per liter; preferably at a rate of from about 5 to about 10 mg per liter so that the measured turbidity does not rise above 20 NTU.

EXAMPLES

The composition and methods set forth herein will be further illustrated in the following, non-limiting Examples. The examples are illustrative of various embodiments only and do not limit the claimed invention regarding the materials, conditions, weight ratios, process parameters and the like recited herein.

Example 1

Analysis of *Pseudomonas* Strain CL145A (ATCC 55799)

The *Pseudomonas* strain CL145A (ATCC 55799) has been further characterized through a polyphasic approach by investigating its phenotypic and genotypic characteristics. The results from the studies disclosed herein indicate that CL145A is a better match to *Pseudomonas protegens*, rather than *Pseudomonas fluorescens*.

Recent developments in the taxonomical study of the genus *Pseudomonas* resulted in the creation of a new species

*Pseudomonas protegens, Pseudomonas protegens* includes several strains formerly identified as *Pseudomonas fluorescens* including strains CHA0, PF, PGNL1, PGNR1, PGNR 2, PGNR 3, PGNR 4, PINR 3 and Pf1. The basis of the reclassification is described by Ramette et al., (2011), and was officially validated in 2012 (Euzeby, 2012). Based on this new information, the best match for CL145A is *Pseudomonas protegens*. MBI-401 will now be identified as *Pseudomonas protegens* strain CL145A (CL145A).

CL145A was characterized through a polyphasic approach investigating phenotypic and genotypic characteristics, as well as confirmation of the presence of two metabolites; 2,4-Diacetylphloroglucinol and Pyoluteorin. Pyoluteorin and 2,4-Diacetylphloroglucinol (see FIG. 3) are central characteristics to the differentiation of *Pseudomonas fluorescens* and *Pseudomonas protegens*. Isolates that do not produce these two compounds, or that only produce one of them, remain known as *Pseudomonas fluorescens*, while *Pseudomonas fluorescens* that produce both compounds have been reclassified as *Pseudomonas* protegens as described by Ramette et al., (2011).

1.1 Analysis of Biochemical, Physiological and Metabolic Characteristics

*Pseudomonas protegens* strain CL145A (ATCC 55799) was subjected to biochemical testing to characterize the isolate and create a baseline for further tracking. As part of this characterization strategy, the growth of CL145A was tested at temperatures of 16° C. and 37° C., and API ZYM and API 20NE assays were performed, which allowed for semiquantitation of enzymatic activities (API ZYM) and identification of Gram-negative non-Enterobacteriaceae (API 20NE). Fatty Acid Profiles and MALDI-TOF profiles were performed as well.

1.1.1 Growth at 16° C. and 37° C.

*Pseudomonas* species are known to grow at a wide range of temperatures, with 28° C. reported as the optimal for many species, and ranging from 4° C. to 45° C. for some species. *Pseudomonas fluorescens* does not grow at 41° C., but some strains show growth as low as 4° C. (Palleroni, 2005).

A dilute cell suspension of CL145A was prepared in phosphate buffer. The suspension was inoculated onto agar plates and incubated overnight at 16° C. and 37° C. Incubators were set at the proper temperatures and allowed to equilibrate overnight before incubations took place. CL145A grew well at both temperatures.

1.1.2. API ZYM

API ZYM provides a platform for rapid semi-quantitation of enzymatic activity. The assay was performed at MBI's facilities, following the manufacturer's directions (Biomerieux). A 1 day PDA plate was inoculated from a glycerol stock of CL145A (ATCC 55799), and incubated overnight at 25° C. Colonies growing on the plate were used to inoculate the API ZYM strip according to manufacturer's instructions, and incubated at 30° C. for 48.5 hours. Results are shown in Table 1 below.

TABLE 1

API ZYM test results for CL145A (ATCC 55799)

| No | Enzyme assayed for | Substrate | pH | Positive | Negative | Rating | Result |
|---|---|---|---|---|---|---|---|
| 1 | Control | | 8.5 | Colorless or color of the sample if it has intense coloration | | 0 | − |
| 2 | Alkaline phosphatase | 2-naphthyl phosphate | 6.5 | Violet | Colorless | 5 | + |
| 3 | Esterase (C 4) | 2-naphythyl butyrate | 7.5 | Violet | or very | 0 | − |
| 4 | Esterase Lipase (C 8) | 2-naphthyl caprylate | 7.5 | Violet | pale | 0 | − |
| 5 | Lipase (C 14) | 2-naphthyl myristate | 7.5 | Violet | yellow | 0 | − |
| 6 | Leucinearylamidase | L-leucyl-2-naphthylamide | 7.5 | Orange | | 4 | + |
| 7 | Valinearylamidase | L-valyl-2-naphthylamide | 7.5 | Orange | | 0 | − |
| 8 | Cysteine arylamidase | L-cystyl-2-naphthylamide | 7.5 | Orange | | 0 | − |
| 9 | Trypsin | N-benzoyl-DL-arginine-2-naphthylamide | 8.5 | Orange | | 0 | − |
| 10 | α-chymotrypsin | N-glutaryl-phenylalanine-2-naphthylamide | 7.5 | Orange | | 0 | − |
| 11 | Acid phosphatase | 2-naphthyl phosphate | 5.4 | Violet | | 5 | + |
| 12 | Naphthol-AS-BI-phosphohydrolase | Naphthol-AS-BI-phosphate | 5.4 | Blue | | 5 | + |
| 13 | α-galactosidase | 6-Br-2-naphthyl-αD-galactopyranoside | 5.4 | Violet | | 0 | − |
| 14 | β-galactosidase | 2-naphthyl-βD-galactopyranoside | 5.4 | Violet | | 0 | − |
| 15 | β-glucuronidase | Naphthol-AS-BI-βD-glucuronide | 5.4 | Blue | | 0 | − |
| 16 | α-glucosidase | 2-naphthyl-αD-glucopyranoside | 5.4 | Violet | | 0 | − |
| 17 | β-glucosidase | 6-Br-2-naphthyl-βD-glucopyranoside | 5.4 | Violet | | 0 | − |
| 18 | N-acetyl-β-glucosaminidase | 1-naphthyl-N-aectyl-βD-glucosaminide | 5.4 | Brown | | 0 | − |
| 19 | α-mannosidase | 6-Br-2-naphthyl-αD-mannopyranoside | 5.4 | Violet | | 0 | − |
| 20 | α-fucosidase | 2-naphthyl-αL-fucopyranoside | 5.4 | Violet | | 0 | − |

The results indicated that CL145A (ATCC 55799) has strong enzymatic activity for acid and alkaline phosphatase, leucine arylamidase and naphtol-AS-BI-phosphohydrolase. Negative results were recorded for all other enzyme tests.

1.1.3. API 20NE

API 20NE allows for semiquantitation of enzymatic activities and identification of Gram-negative non-Enterobacteriaceae. The assay was performed following manufacturer's directions (Biomerieux). A 1 day PDA plate was inoculated from a glycerol stock of CL145A (ATCC 55799), and incubated overnight at 25° C. Colonies growing on the plate were used to inoculate the API 20NE strip according to manufacturer's instructions, and incubated at 30° C. for 48.5 hours. Results are shown in Table 2.

TABLE 2

API 20NE test results for CL145A (ATCC 55799)

| Test | Active Ingredient | Reaction/Enzymes | Negative | Positive | Summary |
|---|---|---|---|---|---|
| NO₃ | Potassium Nitrate | Reduction of nitrates to nitrites | Colorless | Pink-Red | − |
|  |  | Reduction of nitrates to nitrogen | Pink | Colorless | NA |
| TRP | L-tryptophane | Indole production (tryptophan) | Colorless Pale-green/yellow | Pink | − |
| GLU | D-glucose | Fermentation (glucose) | Blue to green | Yellow | − |
| ADH | L-arginine | Arginine Dihydrolase | Yellow | Orange/pink/red | + |
| URE | Urea | Urease | Yellow | Orange/pink/red | + |
| ESC | Esculin ferric citrate | Hydrolysis (β-glucosidase)(esculin) | Yellow | Grey/brown/black | − |
| GEL | Gelatin (bovine origin) | Hydrolysis (protease)(gelatin) | No pigment diffusion | Diffusion of black pigment | + |
| PNPG | 4-nitrophenyl-βD-galactopyranoside | B-galactosidase (Para-nitrophenyl-(βD-galactopyranosidase) | Colorless | Yellow | − |
| |GLU| | D-glucose | Assimilation of glucose | Transparent | Opaque | + |
| |ARA| | L-arabinose | Assimilation of arabinose | Transparent | Opaque | ± |
| |MNE| | D-mannose | Assimilation of mannose | Transparent | Opaque | + |
| |MAN| | D-mannitol | Assimilation of mannitol | Transparent | Opaque | + |
| |NAG| | N-acetyl-glucosamine | Assimilation of n-acetyl-glucosamine | Transparent | Opaque | + |
| |MAL| | D-maltose | Assimilation of maltose | Transparent | Opaque | − |
| |GNT| | Potassium gluconate | Assimilation of potassium gluconate | Transparent | Opaque | + |
| |CAP| | Capric acid | Assimilation of capric acid | Transparent | Opaque | + |
| |ADI| | Adipic acid | Assimilation of adipic acid | Transparent | Opaque | + |
| |MLT| | Malic acid | Assimilation of malate | Transparent | Opaque | + |
| |CIT| | Trisodium citrate | Assimilation of trisodium citrate | Transparent | Opaque | + |
| |PAC| | Phenylacetic acid | Assimilation of phenylacetic acid | Transparent | Opaque | + |
| NO₃ | Potassium Nitrate | Reduction of nitrates to nitrites | Colorless | Pink-Red | − |
|  |  | Reduction of nitrates to nitrogen | Pink | Colorless | NA |
| NO₃ | Potassium Nitrate | Reduction of nitrates to nitrites | Colorless | Pink-Red | − |
|  |  | Reduction of nitrates to nitrogen | Pink | Colorless | NA |
| TRP | L-tryptophane | Indole production (tryptophan) | Colorless Pale-green/yellow | Pink | − |
| GLU | D-glucose | Fermentation (glucose) | Blue to green | Yellow | − |
| ADH | L-arginine | Arginine Dihydrolase | Yellow | Orange/pink/red | + |
| URE | Urea | Urease | Yellow | Orange/pink/red | + |
| ESC | Esculin ferric citrate | Hydrolysis (β-glucosidase)(esculin) | Yellow | Grey/brown/black | − |
| GEL | Gelatin (bovine origin) | Hydrolysis (protease)(gelatin) | No pigment diffusion | Diffusion of black pigment | + |
| PNPG | 4-nitrophenyl-βD-galactopyranoside | B-galactosidase (Para-nitrophenyl-βD-galactopyranosidase) | Colorless | Yellow | − |
| |GLU| | D-glucose | Assimilation of glucose | Transparent | Opaque | + |
| |ARA| | L-arabinose | Assimilation of arabinose | Transparent | Opaque | ± |
| |MNE| | D-mannose | Assimilation of mannose | Transparent | Opaque | + |
| |MAN| | D-mannitol | Assimilation of mannitol | Transparent | Opaque | + |
| |NAG| | N-acetyl-glucosamine | Assimilation of n-acetyl-glucosamine | Transparent | Opaque | + |
| |MAL| | D-maltose | Assimilation of maltose | Transparent | Opaque | − |
| |GNT| | Potassium gluconate | Assimilation of potassium gluconate | Transparent | Opaque | + |

TABLE 2-continued

API 20NE test results for CL145A (ATCC 55799)

| Test | Active Ingredient | Reaction/Enzymes | Negative (Results) | Positive | Summary |
|---|---|---|---|---|---|
| |CAP| | Capric acid | Assimilation of capric acid | Transparent | Opaque | + |
| |ADI| | Adipic acid | Assimilation of adipic acid | Transparent | Opaque | + |
| |MLT| | Malic acid | Assimilation of malate | Transparent | Opaque | + |
| |CIT| | Trisodium citrate | Assimilation of trisodium citrate | Transparent | Opaque | + |
| |PAC| | Phenylacetic acid | Assimilation of phenylacetic acid | Transparent | Opaque | + |
| $NO_3$ | Potassium Nitrate | Reduction of nitrates to nitrites | Colorless | Pink-Red | − |
| | | Reduction of nitrates to nitrogen | Pink | Colorless | NA |
| TRP | L-tryptophane | Indole production (tryptophan) | Colorless Pale-green/yellow | Pink | − |
| GLU | D-glucose | Fermentation (glucose) | Blue to green | Yellow | − |
| ADH | L-arginine | Arginine Dihydrolase | Yellow | Orange/pink/red | + |
| URE | Urea | Urease | Yellow | Orange/pink/red | + |
| ESC | Esculin ferric citrate | Hydrolysis (β-glucosidase)(esculin) | Yellow | Grey/brown/black | − |
| GEL | Gelatin (bovine origin) | Hydrolysis (protease)(gelatin) | No pigment diffusion | Diffusion of black pigment | + |
| PNPG | 4-nitrophenyl-βD-galactopyranoside | B-galactosidase (Para-nitrophenyl-βD-galactopyranosidase) | Colorless | Yellow | − |
| |GLU| | D-glucose | Assimilation of glucose | Transparent | Opaque | + |
| |ARA| | L-arabinose | Assimilation of arabinose | Transparent | Opaque | ± |
| |MNE| | D-mannose | Assimilation of mannose | Transparent | Opaque | + |
| |MAN| | D-mannitol | Assimilation of mannitol | Transparent | Opaque | + |
| |NAG| | N-acetyl-glucosamine | Assimilation of n-acetyl-glucosamine | Transparent | Opaque | + |
| |MAL| | D-maltose | Assimilation of maltose | Transparent | Opaque | − |
| |GNT| | Potassium gluconate | Assimilation of potassium gluconate | Transparent | Opaque | + |
| |CAP| | Capric acid | Assimilation of capric acid | Transparent | Opaque | + |
| |ADI| | Adipic acid | Assimilation of adipic acid | Transparent | Opaque | + |
| |MLT| | Malic acid | Assimilation of malate | Transparent | Opaque | + |
| |CIT| | Trisodium citrate | Assimilation of trisodium citrate | Transparent | Opaque | + |
| |PAC| | Phenylacetic acid | Assimilation of phenylacetic acid | Transparent | Opaque | + |

Key:
+ (Positive),
− (Negative),
± (weak)

*Pseudomonas protegens* does not reduce nitrate. Additionally, Ramette et al. (2011) report that *P. protegens* can assimilate N-acetyl-D-glucosamine, while *P. fluorescens* cannot. CL145A can assimilate N-acetyl-D-glucosamine according to API 20 NE results. CL145A and *P. protegens* also share the ability to assimilate phenyl acetate (*P. fluorescens* cannot). CL145A displayed negative glucuronidase activity in the API ZYM test. *P. protegens* cannot assimilate D-glucuronate, while *P. fluorescens* can assimilate D-glucuronate.

In summary, CL145A (also referred to as ATCC 55799 or MBI-401) shares many phenotypic traits that differentiate it from *P. fluorescens* and indicate closer similarity to *P. protegens*. However, *Pseudomonas* identification based on phenotypic characteristics can be difficult and an ultimate identification always requires a DNA-based approach.

1.1.4. Antibiotic Resistance Profile

One glycerol stock vial of CL145A was equally distributed onto Mueller-Hinton Agar plates (100 μl per plate) and spread on the plate using a sterile cell spreader. Antibiotic discs were then placed onto the plates along with a blank sterile disc. Plates were incubated at 25° C. in the dark for 72 hours. Results are shown in Table 3.

TABLE 3

Antibiotic resistance profile for CL145A (ATCC 55799)

| Antibiotic tested | Concentration (μg) | Suppresses growth of CL145A |
|---|---|---|
| Tetracycline | 30 | No |
| Kanamycin | 30 | Yes |
| Erythromycin | 15 | No |
| Streptomycin | 10 | No |
| Penicillin | 10 | No |
| Ampicillin | 10 | No |
| Oxytetracycline | 30 | Yes |
| Chloramphenicol | 30 | No |

TABLE 3-continued

Antibiotic resistance profile for CL145A (ATCC 55799)

| Antibiotic tested | Concentration (μg) | Suppresses growth of CL145A |
|---|---|---|
| Ciprofloxacin | 5 | Yes |
| Gentamicin | 10 | Yes |
| Piperacillin | 100 | Yes |
| Cefuroxime | 30 | No |
| Imipenem | 10 | Yes |
| Sulphamethoxazole-Trimethoprim | 23.75/25 | Yes |

Figure 3:
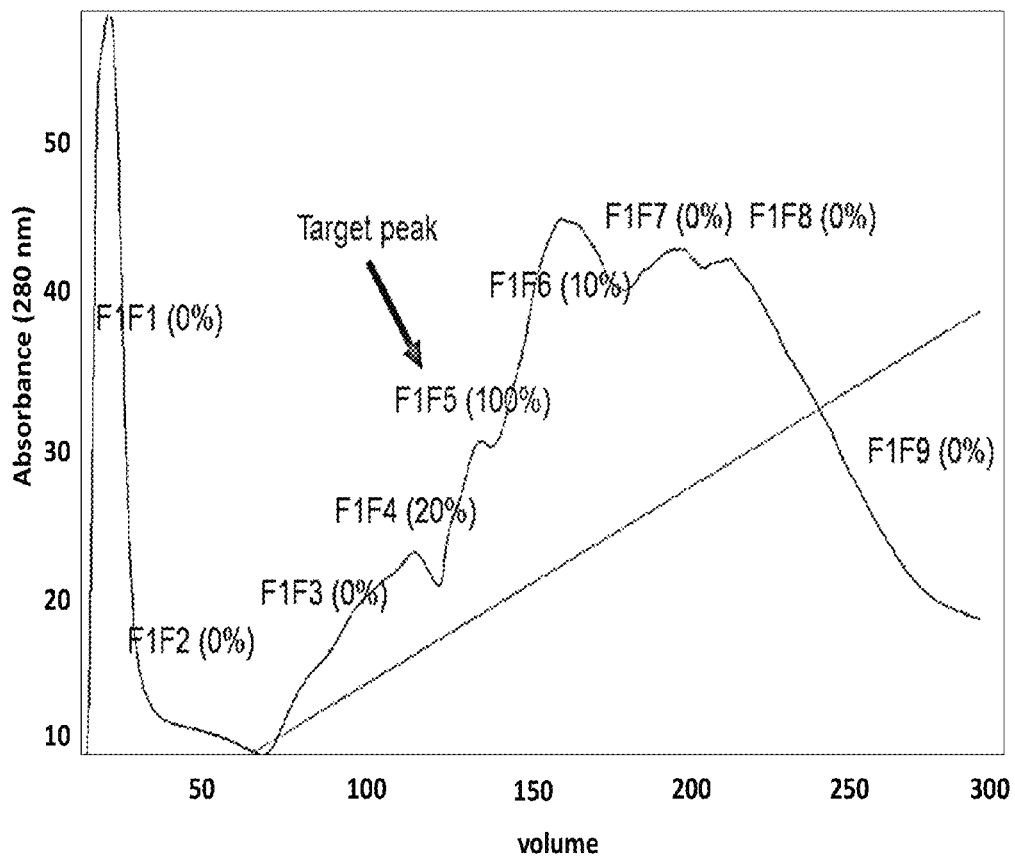
FIG. 3 shows the absorbance spectra (280 nm) of F1 (FIGS. 2 & 3) through HiPrep™ 16/10 Q FF column by low salt loading and the corresponding mussel mortality at $8^{th}$ day (data shown in the parenthesis).

The antibiotic profile results indicated that CL145A is resistant to tetracycline, erythromycin, streptomycin, penicillin, ampicillin, chloramphenicol and cefuroxime as shown in FIG. 3 as growth of CL145A was not inhibited by the antibiotic disc; and shown to be sensitive to kanamycin, oxytetracycline, ciprofloxacin, gentamicin, piperacillin, imipenem and sulphamethoxazole-treimethoprim as growth of CL145A was inhibited following 72 hours incubation.

1.1.5. Analysis of Fatty Acid Methyl Ester Composition (FAME Analysis)

An agar plate with 24-hour old colonies of CL145A was submitted for Fatty Acid Methyl Ester (FAME) profiling to Microbial ID, Inc. (Newark, N.J.). The main fatty acids found are described below in Table 4.

TABLE 4

FAME analysis for CL145A (ATCC 55799)

| Lipid name | % of total |
|---|---|
| Sum In Feature 2 | 0.45 |
| 10:0 | 0.36 |
| 10:0 3OH | 4.74 |
| 14:0 | 0.46 |
| 12:0 | 1.91 |
| Sum In Feature 3 | 32.23 |
| 16:0 | 26.89 |
| 12:0 2OH | 5.15 |
| 12:1 3OH | 1.01 |
| 12:0 3OH | 5.54 |
| 16:1 w5c | 0.11 |
| 17:0 iso | 0.10 |
| 16:0 3OH | 4.41 |
| Sum In Feature 8 | 18.69 |
| 18:0 | 0.65 |
| 18:1 w7c 11-methyl | 0.18 |
| 17:0 | 0.10 |
| 17:0 cyclo | 1.42 |

The FAME profile for CL145A appears to match with a *Pseudomonas putida* biotype A strain in the database, showing the highest similarity index (0.730). The next three best matches were with *Pseudomonas fluorescens* biotype A, biotype B and biotype G, all with similarity indices below 0.700.

1.2. 16S rRNA Gene Amplification and Sequencing 1.2.1 DNA Extraction of CL145A (ATCC 55799)

*Pseudomonas protegens* strain CL145A (ATCC 55799) was streaked on fresh potato dextrose plates and allowed to grow for 2-3 days or until enough biomass was evident. A loopful of the bacterium was suspended in DNA extraction buffer (included in the MoBio Ultra Clean Microbial DNA Extraction Kit, Cat No. 12224-50, Carlsbad, Calif., USA) using a sterile loop. DNA was extracted using the MoBio Ultra Clean Microbial DNA extraction kit using the manufacturer's protocol. DNA extract was checked for quality and quantity by running a 5 μL aliquot on a 1% agarose gel.

1.2.2 PCR amplification of the 16S rRNA gene from CL145A (ATCC 55799)

PCR reactions for the amplification of the 16s rRNA gene were performed by combining 1.5 ul of DNA extract CL145A (ATCC 55799) with 20 μL nuclease-free sterile water, 25 μL GoTaq Green Mastermix (Promega), tL forward primer (SEQ ID NO:1), and 1.5 μL reverse primer (SEQ ID NO:2). The PCR reaction was performed using a thermocycler PCR machine under the following conditions: 10 minutes at 95° C. (initial denaturing), 30 cycles of 45 seconds at 94° C., 45 seconds at 55° C. and 2 minutes at 72° C., followed by 5 minutes at 72° C. (final extension) and a final hold temperature of 10° C. The size, quality and quantity of the PCR product was evaluated by running a 5 uL aliquot on a 1% agarose gel, and comparing the product band to a mass ladder (Hi-Lo mass ladder, Bionexus, Oakland, Calif.).

1.2.3 16S rRNA Sequencing

Excess primers, nucleotides, enzyme and template were removed from the PCR product using the MoBio PCR clean up Kit (Cat No. 12500-50) following the manufacturer's instructions. The cleaned PCR product was subjected to direct sequencing using the primers described above.

1.2.4 Data Analysis

The forward and reverse sequences were aligned using the BioEdit® software, and a consensus sequence was generated for further comparison to sequence databases. The identification of phylogenetic neighbors was initially carried out by the BLASTN (Altschul et al., 1997) program against the database containing type strains with validly published prokaryotic names and representatives of uncultured phylotypes (Kim et al., 2012).

The top thirty sequences with the highest scores were then selected for the calculation of pairwise sequence similarity using global alignment algorithm (Myer & Miller, 1988), which was implemented at the EzTaxon-e server (Kim et al., 2012).

1.2.5 Results

The forward (SEQ ID NO:3) and reverse (SEQ ID NO:4) sequences were used to generate a 1445 base pair consensus sequence (SEQ ID NO:5).

The 16S rRNA gene consensus sequence of CL145A (ATCC 55799) was compared to those available sequences of type strains using EzTaxon-e server.

The search and comparison implements on Ex-Taxon-e server indicated that CL145A (also referred to as ATCC 55799 or MBI-401) was most similar to *Pseudomonas protegens* CHA0$^T$ and in comparison, more distantly related to *Pseudomonas fluorescens*. *Pseudomonas protegens* CHA0$^T$ is the type strain as described by Ramette et al., (2011).

Sequences were downloaded into MEGA5, and aligned using MUSCLE. A Neighbor-Joining tree was built to visualize the relationship of CL145A to the type strain of the genus *Pseudomonas* (FIG. 1). The tree clearly illustrates that CL145A is a strain of *Pseudomonas protegens*, and that *Pseudomonas fluorescens* falls in a more distant and separate branch of the tree.

The evolutionary history was inferred using the Neighbor-Joining method (Saitou and Nei, 1987). The bootstrap consensus tree inferred from 2000 replicates (Felsenstein, 1985) is taken to represent the evolutionary history of the taxa analyzed. Branches corresponding to partitions reproduced in less than 50% bootstrap replicates are collapsed. The percentage of replicate trees in which the associated taxa clustered together in the bootstrap test (2000 replicates) are shown next to the branches (Felsenstein, 1985). The tree is drawn to scale, with branch lengths in the same units as those of the evolutionary distances used to infer the phylogenetic tree. The evolutionary distances were computed using the Jukes-Cantor method (Jukes and Candor, 1969) and are in the units of the number of base substitutions per site. The analysis involved 21 nucleotide sequences. Codon positions included were 1st+2nd+3rd+Noncoding. All ambiguous positions were removed for each sequence pair. There were a total of 1505 positions in the final dataset. Evolutionary analyses were conducted in MEGA5 (Tamura et al., 2011).

Figure 2:
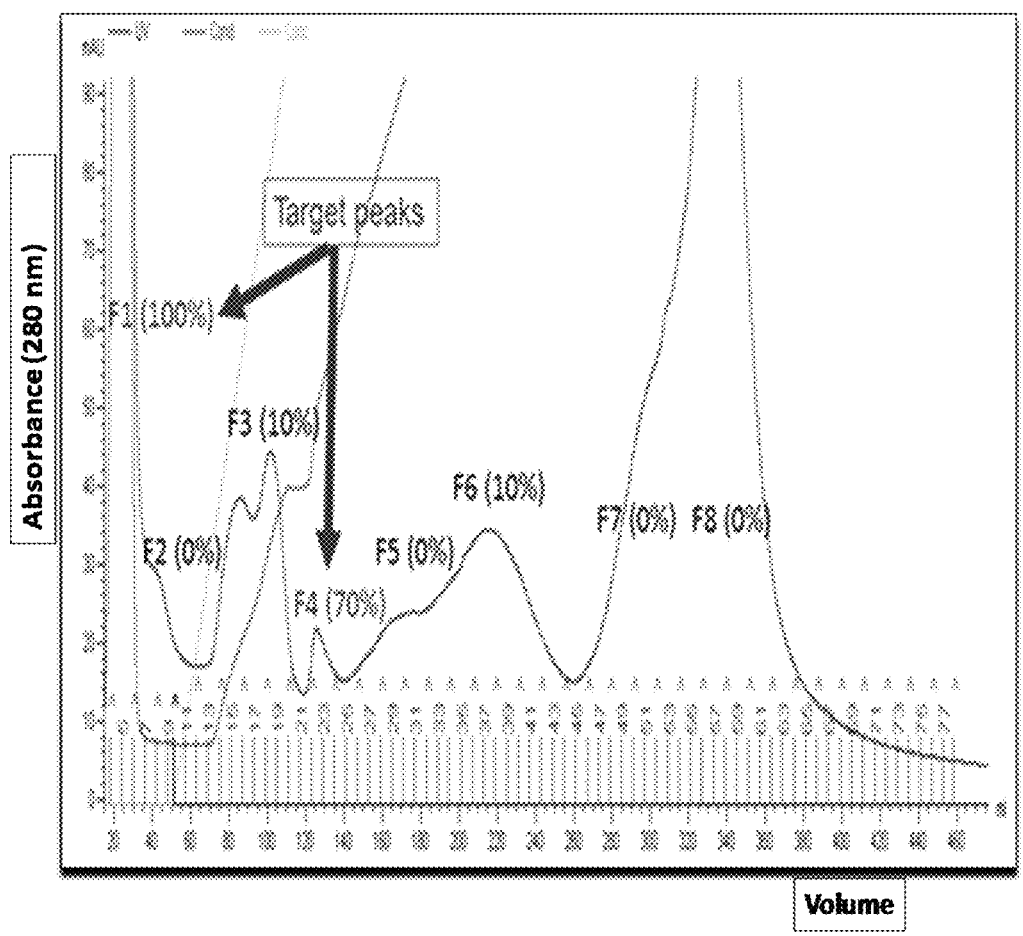
FIG. 2 shows the absorbance spectra (280 nm) of 2.8 M $(NH_4)_2SO_4$ precipitation fraction through HiPrep™ 16/10 Q FF column by high salt loading and the corresponding mussel mortality at $8^{th}$ day (data shown in the parenthesis).

Additionally, comparisons were done with representatives of the bacterial domain using NCBI BLAST and limiting the search to the Reference Sequence Database. In order to confirm that the top matches from NCBI BLAST were actually due to misnaming of Pseudomonas isolates as Pseudomonas fluorescens, the top matches to Pseudomonas fluorescens (strains LMG 5167, Pf-101, Pf-68, CPF-10, 7-1, and LC-G-2) were compared to Pseudomonas protegens in Ez-Taxon to confirm that they were not incorrectly named in the NCBI BLAST database. The sequences were imported into MEGA5, aligned by MUSCLE against CL145A (MBI-401) and Pseudomonas protegens CHA0$^T$ and Pseudomonas fluorescens DSM 50080$^T$*A phylogenetic tree was constructed to evaluate taxonomy (FIG. 2). The phylogenetic tree shown in FIG. 2 illustrates that Pseudomonas strains LMG 5167, Pf-101, Pf-68, CPF-10, 7-1, and LC-G-2 were found to all match to Pseudomonas protegens type strain (CHA0$^T$), and that these strains were grouped together with Pseudomonas protegens strains in the phylogenetic tree. In contrast, the Pseudomonas fluorescens type strain (DSM$^T$) is not in the same group as the Pseudomonas protegens type strain (CHA0$^T$), as both strains are in different branches of the phylogenetic tree. The evolutionary history was inferred using the Neighbor-Joining method (Saitou and Nei, 1997). The bootstrap consensus tree inferred from 2000 replicates (Felsenstein, 1985) is taken to represent the evolutionary history of the taxa analyzed (Felsenstein, 1985). Branches corresponding to partitions reproduced in less than 50% bootstrap replicates are collapsed. The percentage of replicate trees in which the associated taxa clustered together in the bootstrap test (2000 replicates) are shown next to the branches (Felsenstein, 1985). The tree is drawn to scale, with branch lengths in the same units as those of the evolutionary distances used to infer the phylogenetic tree. The evolutionary distances were computed using the Jukes-Cantor method (Jukes and Cantor, 1969) and are in the units of the number of base substitutions per site. The analysis involved 14 nucleotide sequences. Codon positions included were 1st+2nd+3rd+Noncoding. All ambiguous positions were removed for each sequence pair. There were a total of 1515 positions in the final dataset. Evolutionary analyses were conducted in MEGA5 (Tamura et al., 2011).

1.3 Production of Pyoluteorin and 2,4-Diacetylphologlucinol

Ramette et al. (2011) describe the production of two secondary metabolites, pyoluteorin and 2,4-Diacetylphloroglucinol (DAPG), as a major characteristic differentiating Pseudomonas protegens from Pseudomonas fluorescens strains alongside genotypic and phenotypic characterization data. The fluorescent Pseudomonas type strain Pf-5 is known to produce both secondary metabolites, pyoluteorin and DAPG, and this strain was used as the positive control.

CL145A and Pf-5 strains were grown on pyoluteorin production broth enriched with 2% glycerol (PhGly), as described by Wang et al., (2011). The media contains per liter: 3 g NH$_4$NO$_3$, 1 g yeast extract, 1 g KH$_2$PO$_4$, 2 g NaCl, 0.5 g MgSO$_4$ and 1 ml of trace minerals solution. Fermentations were performed in 250 ml Erlenmeyer flasks with 50 ml of media. Incubation was performed at 25° C. and 200 rpm for 48 hours. Fermentations were done side-by-side with CL145A and Pf-5 (NRRL B-23932) and harvested after 48 hours. Due to the lack of commercially available standards for pyoluteorin, strain Pf-5 was used as an internal standard.

The fermentation broths were extracted using Amberlite XAD-7 resin (Asolkar et al., 2006) by shaking the Whole Cell Broth (WCB) with resin at 225 rpm for two hours at room temperature. The resin and cell mass were collected by filtration through cheesecloth and washed with deionized (DI) water to remove salts. The resin, cell mass, and cheesecloth were then soaked for 1 hour in acetone/methanol (1:1) after which the solvent was filtered and dried under vacuum using rotary evaporator to give the crude extract. The crude extracts obtained from the above were dissolved in methanol to get a known concentration (10 mg/mL) which were later analyzed using Liquid chromatography-mass spectrometry (LCMS).

Mass spectroscopy analysis of crude extract samples were performed on a Thermo Finnigan LCQ Deca XP Plus electrospray (ESI) instrument using both positive and negative ionization modes in a full scan mode (m/z 100-1500 Da) and on a LCQ DECA XPplus Mass Spectrometer (Thermo Electron Corp., San Jose, Calif.). Thermo high performance liquid chromatography (HPLC) instrument equipped with a Finnigan Surveyor PDA plus detector, autosampler plus, MS pump and a 4.6 mm×100 mm Luna C18 5 µm column (Phenomenex). The solvent system consisted of water (solvent A) and acetonitrile (solvent B). The mobile phase began at 10% solvent B and is linearly increased to 100% solvent B over 20 min and then kept for 4 min, and finally returned to 10% solvent B over 3 min and kept for 3 min. The flow rate was 0.5 mL/min. The injection volume was 10 µL and the samples were kept at room temperature in an auto sampler. Mass spectroscopy analyses of compounds of interest present in the samples were performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The compounds of interest in this analysis were pyoluteorin (1) and DAPG (2) which were characterized by comparing the UV absorbance profile, retention time (RT) and molecular weight with those of the internal reference standard compounds.

Pyoluteorin (1) and DAPG (2) have been reported as secondary metabolites from Pseudomonas fluorescens Pf-5 (Ramette et al., 2011). As a standard sample of pyoluteorin was not available, the crude extract of Pf-5 was used to identify the production of pyoluteorin in a crude extract of CL145A. Pyoluteorin has a RT of 11:30 min, a molecular mass of 272.02 in positive ionization mode and UV absorption max at 206, 254 & 308 nm. The isotopic spitting pattern in the MS confirms the presence of the two chlorine atoms in the molecule. The standard sample of 2,4-diacetylphloroglucinol (2) was purchased from Santa Cruz Biotechnology (CAS 2161-86-6) and has a RT of 13.99 min, molecular weight of 210.14 and UV absorption max at 204, 268 & 320 nm. The production of both the compounds 1 & 2 were detected with RT 11:30 and 13:96 min respectively in the crude extract of CL145A grown in the fermentation medium containing glycerol, with identical UV and mass spitting pattern to that of standard compounds. The structures for pyoluteorin and DAPG are shown in FIG. 3.

The production of both secondary metabolites pyoluteorin and DAPG by CL145A when grown under specific media, temperature and agitation conditions designed to optimize for the production of said metabolites. Presence of pyoluteorin was confirmed by identification of peaks according to mass spectrum patterns, retention times and UV spectra that are specific to pyoluteorin. The presence of DAPG was further confirmed by comparison to commercial standard.

Batches were produced in media FM3 and DM7 and analyzed as described above. Pyoluteorin and DAPG were not detected in these media under fermentation conditions typical of commercial manufacturing.

1.4 Conclusion

MBI-401, was conclusively identified as *Pseudomonas protegens* strain CL145A. An earlier effort to characterize the microorganism had yielded an identification of *Pseudomonas fluorescens* (Pf). The change in the species identity is the outcome of recent revisions to the taxonomy of *Pseudomonas fluorescens* that grouped several strains previous known as Pf into a new species characterized by divergence of 16S rRNA gene sequences and the production of pyoluteorin and DAPG, as well as other biochemical traits. Therefore, CL145A is now classified as a strain of the newly formed *Pseudomonas protegens* grouping.

Example 2

Isolation of Molluscidal Proteins

Experimental Materials and Methods

The general scheme used is shown in FIG. 1.

Preparation of protein solution

Cell paste of CL145A was homogenized at 10,000 rpm for 2 min in 900 mL of 50 mM of pH 7.4 phosphate buffer. The homogenate was centrifuged at 8000 rpm for 15 min. The precipitate was homogenized and centrifuged again under the same condition. To the combined homogenate (1.8 L) was added 5.4 mL of 40 mM freshly-made PMSF in ethanol (Final concentration of PMSF and ethanol: 0.12 mM and 0.3%, respectively). The resulting solution was stored at 4° C. for 4 hr, and then centrifuged at 8000 rpm for 15 min. The resulting supernatant was used for protein precipitation.

Protein Precipitation by $(NH_4)_2SO_4$

To 1.8 L supernatant was slowly added 190 g $(NH_4)_2SO_4$ by stirring, stored about 10 min at 4° C., centrifuged at 8000 rpm for 15 min. The precipitate was suspended in 45 mL of 50 mM of pH 7.4 phosphate buffer, obtaining 0.8 M $(NH_4)_2SO_4$ precipitated proteins. In a similar means, 166, 166 and 143 g $(NH_4)_2SO_4$ was sequentially added to the homogenate solution respectively, obtaining the corresponding fractions of 1.5, 2.2 and 2.8 M $(NH_4)_2SO_4$ precipitated proteins. They were sequentially suspended in 45, 45 and 25 mL of 50 mM of pH 7.4 phosphate buffer, respectively. After precipitation, the resulting 2.8 M $(NH_4)_2SO_4$ solution was stored at 4° C. overnight. The solution was centrifuged again at 8000 rpm for 15 min at 4° C. The resulting precipitated protein was suspended in 20 mL of 50 mM of pH 7.4 phosphate buffer. All protein fractions were frozen at −20° C. until next step for separation.

Q-Sepharose Ionic Exchange Column

High Salt Loading:

To make all protein bind to the Q-Sepharase column, the active proteins from $(NH_4)_2SO_4$ precipitation were diluted 2 times with 10 mM of pH 7.4 phosphate buffer plus 0.5 M of pH 7.4 sodium chloride solution, loading amount was 10 mL. Buffer A was 10 mM of pH 7.4 sodium phosphate buffer and buffer B was 10 mM phosphate buffer with 1M NaCl. Parameters for running FPLC were following: flow rate (5 mL/min), pressure setting limit (0.5 mPa), starting concentration of %0 of B buffer, column equilibrium (3CV), flow through fractionation (6 mL/tube), sample injection (empty loop 10.5 mL), washing out unbound sample (2CV), elution fraction size (6 mL/tube), linear gradient target B (100%), length of gradient (20 CV), gradient delay (5 mL), clean after elution (3 CV) and UV wavelength (280 nm).

Low Salt Loading:

The flow through fraction from high salt loading was subjected again into Q-sepharose column, the flow through fraction was diluted with 50 mM of pH 7.4 phosphate buffer. Buffer A was 10 mM of pH 7.4 sodium phosphate buffer and buffer B as follows following: flow rate (5 mL/min), pressure setting limit (0.5 mPa), starting concentration of B (0%), column equilibrium (3CV), flow through fractionation (6 mL/tube), sample injection (empty loop 10.5 mL), washing out unbound sample (2CV), elution fraction size (6 mL/tube), linear gradient target B (65%), length of gradient (20 CV), gradient delay (5 mL), clean after elution (3 CV) and UV wavelength (280 nm).

Phenyl HP Column (Self-Made Phenyl HP Column)

A self-made column filled with phenyl sepharose high performance resin [packed volume 22.7 mL (11.3 mm out of 20 mm in 16/20 column) was used for further purification. The active fraction from Q-sepharose low salt loading was diluted with 1M citrate buffer (pH 7.0) before loading. Buffer B was 10 mM of pH 7.4 sodium phosphate buffer and buffer A was 10 mM phosphate buffer with 1M NaCl. Parameters for running FPLC were following: flow rate (5 mL/min), pressure setting limit (0.5 mPa), starting concentration of B (25%), column equilibrium (3CV), flow through fractionation (6 mL/tube), sample injection (empty loop 2.5 mL), washing out unbound sample (2CV), elution fraction size (8 mL/tube), linear gradient target B (100%), length of gradient (25 CV), gradient delay (5 mL), clean after elution (3 CV) and UV wavelength (280 nm). Collection was performed based on the peaks and concentration was carried out by using centrifugal filter unites Amicon® Ultra (Millipore Ireland Ltd., Carrigtwohill Co, Cork IRL).

Butyl HP Column (5 mL)

The impure peaks from Phenyl HP columns were subjected to butyl HP column again. The parameters for running Butyl HP columns were exact same as Phenyl HP column.

Gel Fixing, Staining and De-Staining

Gel fixing solution consists of 50% methanol, 10% acetic acid and 40% water. It usually takes 1 hr for gel fixing on the shaking condition (Orbit™ LS slow speed shaker, Labnet International, Inc.). Gel staining solution consists of 0.25% Brilliant Blue R-250, 10% acetic acid and 89.75% water. It usually takes 1 hr for gel staining on the shaking condition. Gel de-staining solution consists of 5% methanol, 7.5% acetic acid and 87.5% water. It usually takes from a few hours to overnight to de-stain the gel.

Native Electrophoresis

Samples were prepared by mixing the following items: The ratio of protein sample maximal volume and native Tris-Glycine sample buffer (2×, Novex® Cat No LC2673) was 1:1. The mixture was centrifuged at 3000 rpm for 1 min. All of each sample was loaded into a gel channel. A standard marker (NativeMark® unstained protein standard, Invitrogen®, Cat No: LC0725). Novex® Tris-Glycine Native running buffer 1× was diluted from 10× (Invitrogen®, Cat No: LC2672). The gel was run for 90 min at 125 V. The gel was fixed, stained and de-stained as the normal procedures as described above.

SDS-PAGE Electrophoresis

Samples were prepared by mixing the following items: Protein sample maximal volume 17 μL, sample reducing agent (3 μL of 10×, Invitrogen® Cat No NP0009) and Tris-Glycine SDS sample buffer (15 μL of 2×, Novex® Cat No LC2676). The mixture was heated for 10 min in boiling water bath. The samples were cooled and centrifuged at 3000 rpm for 1 min. All of each sample was loaded into a gel channel (NuPAGE® 10% Bis-Tris Gel, 1.0 mm×10 well, Invitrogen™, Cat No: NP0301BOX). A standard marker (SeeBlue® plus 2 pre-stained standard 1× Invitrogen™, Cat No: LC5925). NuPAGE® MOPS SDS Running buffer 1× was diluted from 20× (Invitrogen®, Cat No: NP0001). The gel was run for 50 min at 200 V. The gel was fixed, stained and de-stained as the normal procedures as described above.

Isoelectric Focusing (IEF) Electrophoresis

Samples were prepared with a ratio of 1:1 mixture between protein samples and Novex® IEF pH 3-7 sample buffer (2×). Each sample with loading buffer (30 μL) was loaded into gel channel (pH 3-7 IEF gel, 1.0 mm×12 wells, Invitrogen®, Cat No: EC66452Box). IEF markers pI 3-10 (Serva Liquid Mix Cat No: 39212) was used as standards. NOVEX® IEF anode (lower) buffer (50×, Invitrogen®, Cat No: LC5300) was diluted in 1×. NOVEX® IEF cathode (upper, i.e., between 2 gel channel) buffer (10×, Invitrogen®, Cat No: LC5370) was diluted in 1×. IEF gel was run at 200 V for 50 min. Then, the gel was fixed, stained and de-stained as the standard procedures described as above.

Protein Determination

Protein concentration was determined by the Bradford method. In brief, Bovine Serum Albumin Standards (2 mg/mL, Fisher Scientific, USA) was diluted with 50 mM pH 7.4 sodium phosphate buffer into a series of concentrations (0.5, 0.4, 0.3, 0.2, 0.1 and 0.05 mg/mL). Ten microliter protein solution (10 μL) was used for each well. The commercial dye solution was diluted with 50 mM of pH 7.4 phosphate buffer by 5 times. This diluted dye solution (190 μL) was added for each well. Plate was incubated 5 min at room temperature after automatic shaking in spectrophotometer. Plate was read at 590 nm by end-point assay.

Mussel Bioassay

Mussel bioassays were performed in twenty milliliter scintillation vials. Ten small mussels (approximately 1 cm long) were incubated in the mussel water (10 mL) for 24 hr first, then the mussel water (10 mL) was changed freshly before test cell lysis was added. Cell lysis or proteins (maximal 500 μL) was added into each vial. After 24 hr, the mussel water with cell lysis or proteins was changed with clean mussel water. Then, mussel water was changed every 24 hr with clean mussel water. Dead mussels were taken away every day and mussel mortality was calculated by number of dead mussel divided by the number of total mussels.

Results and Discussion

Preparation of Protein Solution

There are many methods for the lysis bacterial cells to release proteins. These methods include mechanical (e.g., homogenization, grinding), physical (e.g., freeze/thaw, high pressure), chemical (e.g., detergents) and biochemical (e.g., lysozyme, glycanase, Dnase) methods. Usually, combined methods are used for protein extraction from bacterial cells. Among these method, most effective and widely used methods are French Pressure cell press (i.e., higher pressure combined with mechanical process), homogenization or sonication with enzymes (e.g., lysozymes, or glycanases, or DNase) or with detergents. In our study, homogenization with and without detergents (e.g., Triton X-100, alkyl-D-glucosides), sonication with and without detergents (e.g., Triton X-100, alkyl-D-glucosides) were tried before. Although these detergents could help to dissolve and stabilize membrane proteins, they are highly potent to mussel ($LC_{50}$<100 ppm). Detergents were not used any more. Sonication with enzymes (e.g., lysozymes) will be used in the next experiment. In this experiment, homogenization was used for protein extraction, and obtained 2.0% protein on the basis of wet cell paste. The scheme used to obtain active proteins is shown in FIG. 1.

Protein Precipitation

Fractions from ammonium sulfate precipitation were submitted to bioassay. Results indicated that fractions including 0.8, 1.5, 2.2, 2.8 and 2.8 (2) M, corresponding to 9.8%, 16.5%, 22.5% and 27% of $(NH_4)_2SO_4$ saturation, respectively, were active against mussel. However, major activity and proteins existed in the 1.5 and 2.2 M $(NH_4)_2SO_4$ precipitation fractions.

Q-Sepharose Ionic Exchange Column

High Salt Loading:

At 280 nm, absorbance spectra of multiple active fractions from $(NH_4)_2SO_4$ precipitation through Q-sepharose FF column by high salt loading was very similar to that of 2.8 M $(NH_4)_2SO_4$ precipitation fraction (FIG. 2), differentiating from the relative abundance of each peak. Mussel mortality in parenthesis of each peak label (FIG. 2) indicated that active proteins existed in two peaks (F1 and F4).

Figure 4:
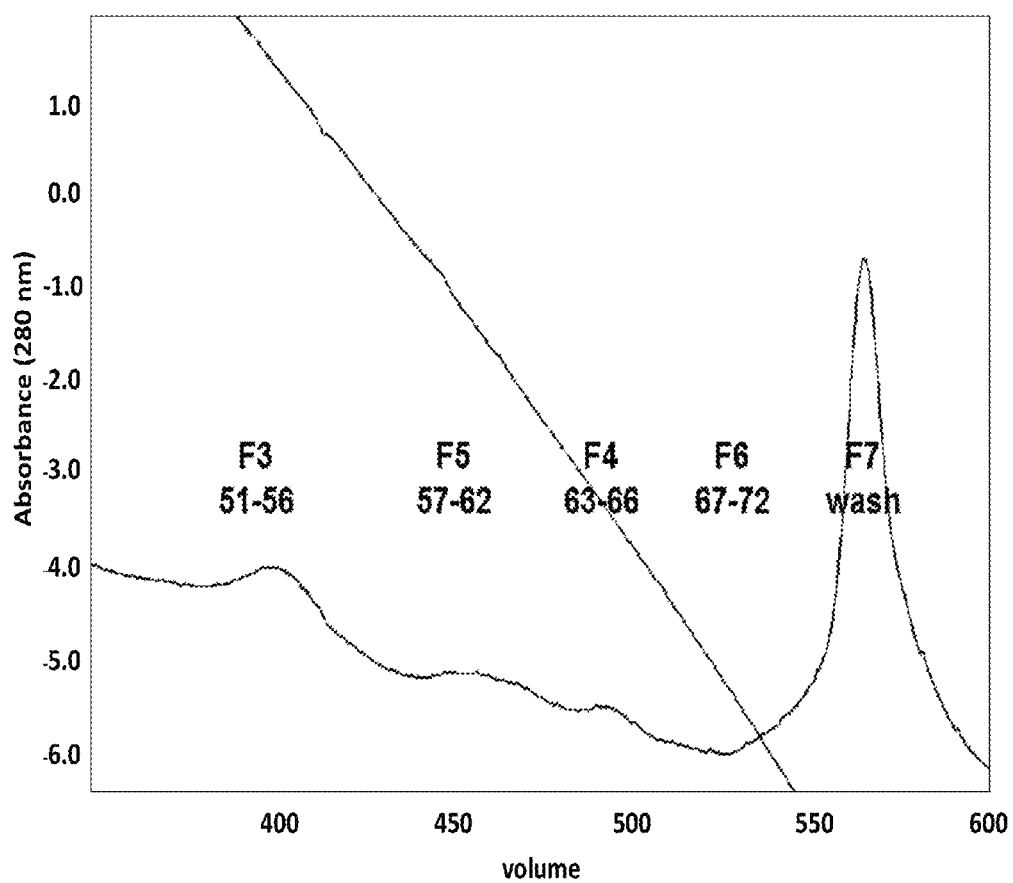
FIG. 4 shows the absorbance spectrum (280 nm) of Active protein fraction F1F5 through Phenyl HP column.

Low Salt Loading:

An absorbance spectrum of F1 at 280 nm of fractions from a Q-Sepharose FF column by low salt loading is shown in FIG. 3. This is a typical spectrum for all flow through fractions from HiPrep™ 16/10 Q FF column by high salt loading. They abundance differs in each peak. Mussel mortality in parenthesis of each peak label (FIG. 4) indicates that active proteins predominantly exists in Fraction F1F5.

Characterization of Active Proteins by Gel Electrophoresis

To distinguish protein fractions from different injections, native, SDS and IEF electrophoresis were performed. Active protein A predominantly came from F4 (FIG. 2). After gel analysis, proteins A, B (F2), F3, F4, F5 and F6 were dosed for mussel bioassay and results (Table 61) indicated that both A and B (F2) were active. Other dosed fractions were inactive. Due to protein limitation, dose-mortality relationship could not be done. This was why I have to scale up.

TABLE 6

Characterization of proteins
A and B by mussel bioassay

| Protein | Concentration (ppm) | Mussel mortality at $7^{th}$ day |
|---|---|---|
| A | 5 | 50% |
| B (F2) | 4 | 60% |

Protein Identification

After proteins A and B were verified to be active in mussel bioassay, their bands on SDS gel were cut and sent out for sequence at UCD genomic center. Results indicated that Protein A is dihydrolipoamide dehydrogenase and protein B is fumarate hydratase Class II (or fumarase). Based on their partial protein sequences and genomic database of Pseudomonas CL 145A, (ATCC 55799) their DNA and whole protein sequences are obtained.

Protein Verification

Figure 6:
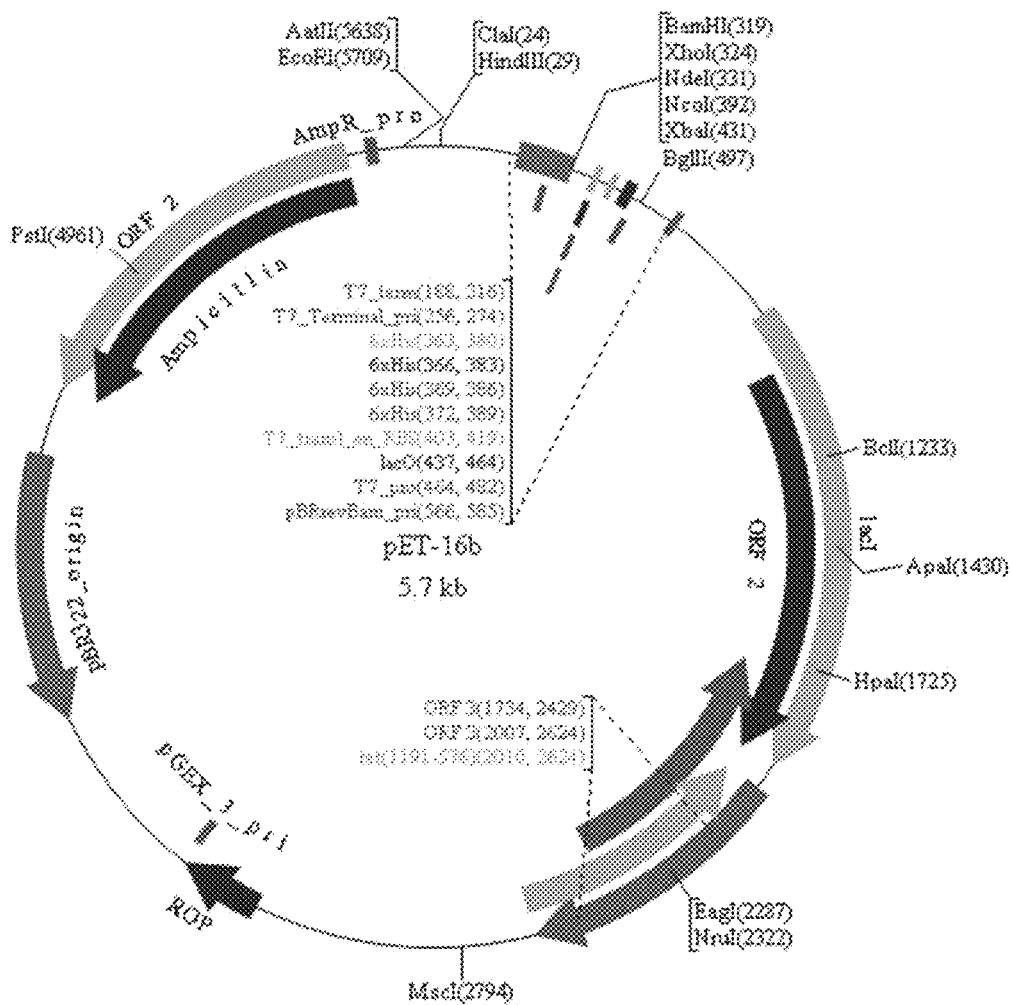
FIG. 6 shows the vector used to clone DNA sequences encoding fumarate hydratase and dihyrolipoamide dehydrogenase.

The verification of protein sequence is undertaken by cloning DNA sequences encoding proteins A and B into the pET21a(Amp) vector (see FIG. 6). The DNA sequences are verified by digesting the plasmid with restriction enzymes NdeI and XhoI. E. coli is chosen as protein expression system. The expressed proteins is verified by protein sequences and protein size on SDS gel.

Phenyl and Butyl HP Columns

The active fraction F1F5 from a Q sepharose FF column with low salt loading was subjected to Phenyl HP column. The absorbance spectrum at 280 nm is shown FIG. 6. The fractions F6 (67-72) and F7 (wash) in the FIG. 6 was combined and concentrated, then subjected to Butyl HP column, yielding active protein B (Wells F1, F2 and F7 in FIGS. 8-10). The fractions F4 and F5 (FIG. 6) were combined and concentrated, then subjected to Butyl HP column, yielding a little active protein A (This is not shown in scheme FIG. 1).

Figure 5:
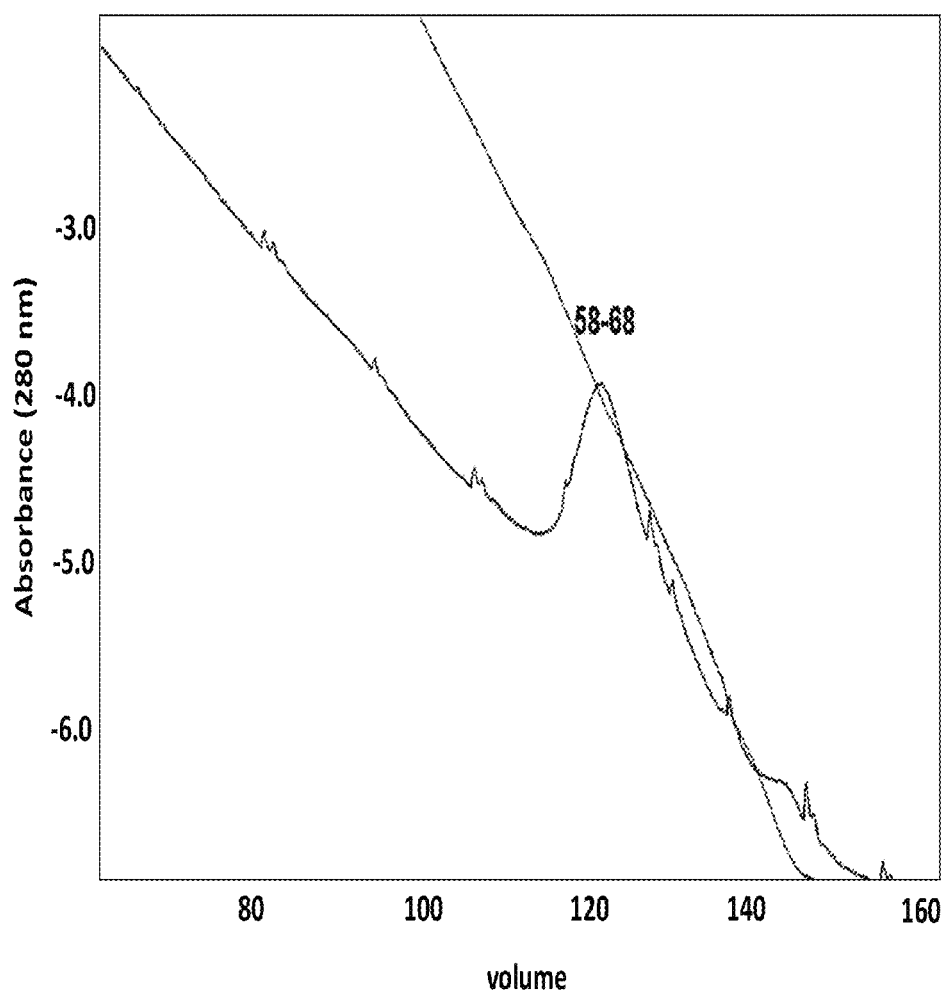
FIG. 5 shows the absorbance spectrum (280 nm) of Active protein A from F1 (FIG. 2) through butyl HP column.

The fraction F4 (FIGS. 2 and 3) was applied to a Butyl HP column; the absorbance spectrum (280 nm) is shown in FIG. 5. The major peak (tube 58-68) was concentrated and produced as active protein A.

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

What is claimed is:

1. A method for controlling molluscs in a location that is a liquid where control is desired comprising: administering an amount of an enzyme having dihydrolipoamide dehydrogenase activity and/or an enzyme having fumarate hydratase activity effective to control said mollusk at said location.

2. The method according to claim 1, wherein said liquid is a body of water or paint.

3. The method according to claim 1, wherein said enzyme having fumarate hydratase activity has at least about 80% homology to the amino acid sequence set forth in SEQ ID NO:6.

4. The method according to claim 1, wherein enzyme having fumarate hydratase activity is encoded by a nucleic acid sequence that has at least about 80% homology to the nucleic acid sequence set forth in SEQ ID NO:7.

5. The method according to claim 1, wherein said enzyme having dihyrolipoamide dehydrogenase activity has at least about 80% homology to the amino acid sequence set forth in SEQ ID NO:8.

6. The method according to claim 1, wherein enzyme having dihyrolipoamide dehydrogenase activity is encoded by a nucleic acid sequence that has at least about 80% homology to the nucleic acid sequence set forth in SEQ ID NO:9.

* * * * *

SEQUENCE LISTING

```
<160> NUMBER OF SEQ ID NOS: 9

<210> SEQ ID NO 1
<211> LENGTH: 20
<212> TYPE: DNA
<213> ORGANISM: Unknown
<220> FEATURE:
<223> OTHER INFORMATION: Forward Primer FD1 5' - 3'

<400> SEQUENCE: 1
agagtttgat cctggctcag                                                  20

<210> SEQ ID NO 2
<211> LENGTH: 17
<212> TYPE: DNA
<213> ORGANISM: Unknown
<220> FEATURE:
<223> OTHER INFORMATION: Reverse Primer RD1, 5' - 3'

<400> SEQUENCE: 2
aaggaggtga tccagcc                                                     17

<210> SEQ ID NO 3
<211> LENGTH: 1216
<212> TYPE: DNA
<213> ORGANISM: Unknown
<220> FEATURE:
<223> OTHER INFORMATION: CL145A (ATCC 55799) FD1 Forward Sequence

<400> SEQUENCE: 3
catgcaagtc gagcggcagc acgggtactt gtacctggtg gcgagcggcg gacgggtgag      60
taatgcctag gaatctgcct agtagtgggg gataacgtcc ggaaacgggc gctaataccg     120
catacgtcct acgggagaaa gtgggggatc ttcggacctc acgctattag atgagcctag     180
gtcggattag ctagttggtg aggtaatggc tcaccaaggc gacgatccgt aactggtctg     240
agaggatgat cagtcacact ggaactgaga cacggtccag amtcctacgg gaggcagcag     300
tggggaatat tggacaatgg gcgaaagcct gatccagcca tgccgcgtgt gtgaagaagg     360
tcttcggatt gtaaagcact ttaagttggg aggaagggca gttacctaat acgtgattgt     420
tttgacgtta ccgacagaat aagcaccggc taactctgtg ccagcagccg cggtaataca     480
gagggtgcaa gcgttaatcg gaattactgg gcgtaaagcg cgcgtaggtg gtttgttaag     540
ttggatgtga aagcccgggg ctcaacctgg gaactgcatc caaaactggc aagctagagt     600
atggtagagg gtggtggaat ttcctgtgta gcggtgaaat gcgtagatat aggaaggaac     660
accagtggcg aaggcgacca cctggactga tactgacact gaggtgcgaa agcgtgggga     720
gcaaacagga ttagataccc tggtagtcca cgccgtaaac gatgtcaact agccgttggg     780
```

-continued

| | |
|---|---|
| agccttgagc tcttagtggc gcagctaacg cattaagttg accgcctggg gagtacggcc | 840 |
| gcaaggttaa aactcaaatg aattgacggg ggcccgcaca gcggtggag catgtggttt | 900 |
| aattcgaagc aacgcgaaga accttaccag gccttgacat ccaatgaact ttctagagat | 960 |
| agattggtgc cttcgggaca ttgagacagg tgctgcatgg ctgtcgtcag ctcgtgtcgt | 1020 |
| gagatgttgg ttaagtccgt acgagcgcac ccttgtctag ttacagcacg tatggtkggc | 1080 |
| actctagaga ctgcgtgaca acggagaaag gkggatgacg tcagtcatca tgcctacgcc | 1140 |
| tgggctacca cgtgctacat gtcggtacag gttgcaagcc gargkgacta atccataaat | 1200 |
| cgatcgtagt ccggac | 1216 |

<210> SEQ ID NO 4
<211> LENGTH: 1146
<212> TYPE: DNA
<213> ORGANISM: Unknown
<220> FEATURE:
<223> OTHER INFORMATION: CL145A (ATCC 55799) RD1 Reverse Sequence Listing

<400> SEQUENCE: 4

| | |
|---|---|
| gttcgacttc ccccagtcat gaatcacacc gtggtaaccg tcctcccgaa ggttagacta | 60 |
| gctacttctg gtgcaaccca ctcccatggt gtgacgggcg gtgtgtacaa ggcccgggaa | 120 |
| cgtattcacc gcgacattct gattcgcgat tactagcgat tccgacttca cgcagtcgag | 180 |
| ttgcagactg cgatccggac tacgatcggt tttatgggat tagctccacc tcgcggcttg | 240 |
| gcaacccttt gtaccgacca ttgtagcacg tgtgtagccc aggccgaaag ggccatgatg | 300 |
| acttgacgtc atccccacct tcctccggtt tgtcaccggc agtctcctta gagtgcccac | 360 |
| cataacgtgc tggtaactaa ggacaagggt tgcgctcgtt acgggactta acccaacatc | 420 |
| tcacgacacg agctgacgac agccatgcag cacctgtctc aatgttcccg aaggcaccaa | 480 |
| tctatctcta gaaagttcat tggatgtcaa ggctggtaa ggttcttcgc gttgcttcga | 540 |
| attaaaccac atgctccacc gcttgtgcgg gccccgtca attcatttga gttttaacct | 600 |
| tgcggccgta ctccccaggc ggtcaactta atgcgttagc tgcgccacta agagctcaag | 660 |
| gctcccaacg gctagttgac atcgtttacg gcgtggacta ccagggtatc taatcctgtt | 720 |
| tgctccccac gctttcgcac ctcagtgtca gtatcagtcc aggtggtcgc cttgccact | 780 |
| ggtgttcctt cctatatcta cgcatttcac cgctacacag gaaattccac caccctctac | 840 |
| catactctag cttgccagtt ttggatgcag ttcccaggtt gagcccgggg ctttcacatc | 900 |
| caacttaaca aaccacctac gcgcgcttta cgcccagtaa ttccgattaa cgcttgcacc | 960 |
| ctctgtatta ccgcggctgc tgggcacaga gttagccggt gcttatttct gtcggtacgt | 1020 |
| caaaacatca cgtattaggt aactgccctt ctccacttaa agtgctttac atcgagactc | 1080 |
| tcacacacgc gcatgctgga gaaatcagct ttcgccattg gtccaatatt ccccactgct | 1140 |
| gcttcg | 1146 |

<210> SEQ ID NO 5
<211> LENGTH: 1445
<212> TYPE: DNA
<213> ORGANISM: Unknown
<220> FEATURE:
<223> OTHER INFORMATION: CL145A (ATCC 55799) Consensus Sequence

<400> SEQUENCE: 5

| | |
|---|---|
| catgcaagtc gagcggcagc acgggtactt gtacctggtg gcgagcggcg gacgggtgag | 60 |
| taatgcctag gaatctgcct agtagtgggg gataacgtcc ggaaacgggc gctaataccg | 120 |

```
catacgtcct acgggagaaa gtggggatc ttcggacctc acgctattag atgagcctag    180
gtcggattag ctagttggtg aggtaatggc tcaccaaggc gacgatccgt aactggtctg    240
agaggatgat cagtcacact ggaactgaga cacggtccag amtcctacgg gaggcagcag    300
tggggaatat tggacaatgg gcgaaagcct gatccagcca tgccgcgtgt gtgaagaagg    360
tcttcggatt gtaaagcact ttaagttggg aggaagggca gttacctaat acgtgattgt    420
tttgacgtta ccgacagaaa taagcaccgg ctaactctgt gcccagcagc cgcggtaata    480
cagagggtgc aagcgttaat cggaattact gggcgtaaag cgcgcgtagg tggtttgtta    540
agttggatgt gaaagccccg ggctcaacct gggaactgca tccaaaactg gcaagctaga    600
gtatggtaga gggtggtgga atttcctgtg tagcggtgaa atgcgtagat ataggaagga    660
acaccagtgg cgaaggcgac cacctggact gatactgaca ctgaggtgcg aaagcgtggg    720
gagcaaacag gattagatac cctggtagtc cacgccgtaa acgatgtcaa ctagccgttg    780
ggagccttga gctcttagtg gcgcagctaa cgcattaagt tgaccgcctg gggagtacgg    840
ccgcaaggtt aaaactcaaa tgaattgacg ggggcccgca caagcggtgg agcatgtggt    900
ttaattcgaa gcaacgcgaa gaaccttacc aggccttgac atccaatgaa ctttctagag    960
atagattggt gccttcggga acattgagac aggtgctgca tggctgtcgt cagctcgtgt   1020
cgtgagatgt tgggttaagt cccgtaacga gcgcaaccct tgtccttagt taccagcacg   1080
ttatggtggg cactctaagg agactgccgg tgacaaaccg gaggaaggtg gggatgacgt   1140
caagtcatca tggcccttc ggcctgggct acacacgtgc tacaatggtc ggtacaaagg   1200
gttgccaagc cgcgaggtgg agctaatccc ataaaaccga tcgtagtccg gatcgcagtc   1260
tgcaactcga ctgcgtgaag tcggaatcgc tagtaatcgc gaatcagaat gtcgcggtga   1320
atacgttccc gggccttgta cacaccgccc gtcacaccat gggagtgggt tgcaccagaa   1380
gtagctagtc taaccttcgg gaggacggtt accacggtgt gattcatgac tggggaagt   1440 cgaac                                                              1445
```

<210> SEQ ID NO 6
<211> LENGTH: 458
<212> TYPE: PRT
<213> ORGANISM: Unknown
<220> FEATURE:
<223> OTHER INFORMATION: Fumarate hydratase

<400> SEQUENCE: 6

Met Ser Asn Thr Arg Ile Glu Arg Asp Ser Met Gly Glu Leu Gln Val
1               5                   10                  15

Pro Glu Gln Ala Leu Tyr Gly Ala Gln Thr Gln Arg Ala Val Asp Asn
            20                  25                  30

Phe Pro Ile Ser Gly Gln Arg Met Pro Ala Ala Phe Ile Arg Ala Leu
        35                  40                  45

Ile Leu Ala Lys Ala Ala Ala Ala Glu Ala Asn Val Glu Leu Gly Gln
    50                  55                  60

Leu Ser Ala Ser Gln Gly Lys Ala Ile Val Asp Ala Ala Gln Gly Leu
65                  70                  75                  80

Leu Glu Gly Asp Tyr Met Gln His Phe Pro Val Asp Ile Phe Gln Thr
                85                  90                  95

Gly Ser Gly Thr Ser Ser Asn Met Asn Ala Asn Glu Val Leu Ala Thr
            100                 105                 110

Leu Ala Ser Arg Leu Leu Gly Glu Pro Val Asn Pro Asn Asp His Val
        115                 120                 125

Asn Cys Gly Gln Ser Ser Asn Asp Ile Ile Pro Thr Thr Ile His Val
    130                 135                 140

Ser Ala Ala Leu Thr Leu His Glu Gln Leu Leu Pro Ala Leu Val His
145                 150                 155                 160

Leu Val Glu Val Ile Glu Arg Lys Ala Val Gln Val His Pro Phe Ile
                165                 170                 175

Lys Thr Gly Arg Thr His Leu Met Asp Ala Met Pro Val Arg Met Ser
            180                 185                 190

Gln Val Leu Asp Gly Trp Ala Gln Gln Leu Lys Ala Asn Ile Ala His
        195                 200                 205

Leu Gln Asp Leu Leu Pro Ser Leu Gln Ala Leu Ala Gln Gly Gly Thr
    210                 215                 220

Ala Val Gly Thr Gly Ile Asn Ala His Pro Glu Phe Ala Ala Arg Phe
225                 230                 235                 240

Ser Arg Gln Leu Ser Lys Leu Thr Gln Val Gln Phe Thr Pro Gly Lys
                245                 250                 255

Asn Leu Phe Ala Leu Ile Gly Ser Gln Asp Thr Ala Val Thr Val Ser
            260                 265                 270

Gly Gln Leu Lys Ala Thr Ala Val Ser Leu Met Lys Ile Ala Asn Asp
        275                 280                 285

Leu Arg Trp Met Asn Ser Gly Pro Leu Ala Gly Leu Gly Glu Ile Glu
    290                 295                 300

Leu Glu Gly Leu Gln Pro Gly Ser Ser Ile Met Pro Gly Lys Val Asn
305                 310                 315                 320

Pro Val Ile Pro Glu Ala Val Ala Met Val Ala Ala Gln Val Ile Gly
                325                 330                 335

Asn Asp Ser Thr Ile Thr Val Ala Gly Gln Ser Gly Asn Phe Glu Leu
            340                 345                 350

Asn Val Met Leu Pro Ile Ile Ala Gln Asn Leu Leu Gly Ser Ile Glu
        355                 360                 365

Leu Leu Ala Asn Ser Ser Arg Leu Leu Ala Asp Lys Ala Ile Ala Ser
    370                 375                 380

Phe Lys Val Asn Glu Pro Lys Leu Lys Glu Ala Leu Ser Arg Asn Pro
385                 390                 395                 400

Ile Leu Val Thr Ala Leu Asn Pro Ile Ile Gly Tyr Gln Lys Ala Ala
                405                 410                 415

Glu Ile Ala Lys Thr Ala Tyr Arg Gln Gly Arg Pro Val Ile Asp Val
            420                 425                 430

Ala Leu Glu Leu Thr Asp Leu Pro Arg Ser Gln Leu Glu Val Leu Leu
        435                 440                 445

Asp Pro Glu Lys Leu Thr Ala Gly Gly Val
    450                 455

<210> SEQ ID NO 7
<211> LENGTH: 1377
<212> TYPE: DNA
<213> ORGANISM: Unknown
<220> FEATURE:
<223> OTHER INFORMATION: Fumarate hydratase nucleic acid sequence

<400> SEQUENCE: 7
atgagtaata cccgtatcga acgcgacagc atgggcgaac tgcaggtccc tgagcaggcc    60
ttgtatggcg cgcagactca gcgcgcggtg gataactttc ccatcagcgg caacgcatg    120 ccggcagcct tcattcgtgc cctgattctg gccaaggctg cagcggccga ggccaacgtc    180

-continued

```
gagcttgggc agctcagcgc gtcccagggc aaggccattg tcgatgccgc ccaggggctg    240
ttggaaggcg actacatgca gcactttccg gtggacatct tccagaccgg ctccggtacc    300
agttccaaca tgaacgccaa cgaagtgctg gcgaccttgg ccagccgcct gttgggcgag    360
ccggtcaatc ccaatgacca cgtcaactgt ggtcagagca gcaacgacat cattcccacc    420
accattcacg tcagcgcagc cctgaccctg catgagcaac tgctgccggc actggtgcac    480
ctggtggagg tcatcgaacg caaggcggtg caggtgcatc ccttcatcaa gaccggtcgt    540
acccacctga tggatgccat gccggtgcga atgagccagg tgctggacgg ttgggcgcag    600
cagctcaagg ccaatatcgc tcacttgcag gacctgctgc cgagcctgca ggccctggct    660
cagggcggca ccgccgtggg gactggaatc aacgctcacc ccgagttcgc tgcgcgcttc    720
agccggcagt tgagcaagct gacccaggtg cagttcaccc cgggcaagaa cctgttcgcc    780
ctgatcggct cacaggacac ggcggtcacg gtgtccggcc agctcaaggc cactgcggtg    840
tcgttgatga agatcgccaa cgacctgcgc tggatgaact ccggtccact ggcggggctt    900
ggcgagatcg agctggaggg gctgcagccg ggctcgtcga tcatgccggg caaggtcaat    960
ccggtgattc cggaagccgt ggcgatggtc gcggcccaag tcattggtaa cgacagcacc    1020
atcaccgtgg ccgggcaatc gggcaacttc gagctcaacg tgatgctgcc gatcattgcc    1080
cagaacctgc tcggcagtat tgaactgctg gccaactcca gtcgcctgtt ggcggacaag    1140
gccattgcca gcttcaaggt caacgagccc aagctcaagg aagcactgtc acgcaacccg    1200
atcctggtga ctgctctgaa cccgatcatc gggtatcaga aggccgctga aattgccaag    1260
actgcctaca ggcaaggtcg cccggtgatc gacgtggcac ttgaactcac tgatctgcca    1320
cgcagccagc ttgaggtcct gctggacccg gaaaaactca ccgcaggcgg cgtgtaa      1377
```

<210> SEQ ID NO 8
<211> LENGTH: 478
<212> TYPE: PRT
<213> ORGANISM: Unknown
<220> FEATURE:
<223> OTHER INFORMATION: 2 dihydrolipoamide dehydrogenase amino acid
      sequence

<400> SEQUENCE: 8

```
Met Thr Gln Lys Phe Asp Val Val Ile Gly Ala Gly Pro Gly Gly
1               5                   10                  15

Tyr Val Ala Ala Ile Lys Ala Ala Gln Leu Gly Leu Thr Thr Ala Cys
            20                  25                  30

Ile Glu Lys Tyr Thr Asp Lys Glu Gly Lys Leu Ala Leu Gly Gly Thr
        35                  40                  45

Cys Leu Asn Val Gly Cys Ile Pro Ser Lys Ala Leu Leu Asp Ser Ser
    50                  55                  60

Trp Lys Phe His Glu Ala Gln Asp Gly Phe Ala Ile His Gly Ile Ser
65                  70                  75                  80

His Ala Gly Val Thr Met Asp Val Pro Ala Met Val Gly Arg Lys Ala
                85                  90                  95

Asn Ile Val Lys Gly Leu Thr Ser Gly Val Ala Thr Leu Phe Lys Ala
            100                 105                 110

Asn Gly Val Thr Ser Ile Gln Gly His Gly Lys Leu Leu Ala Gly Lys
        115                 120                 125

Lys Val Glu Val Thr Lys Pro Asp Gly Ser Val Glu Val Ile Glu Ala
    130                 135                 140

Glu Asn Val Ile Leu Ala Pro Gly Ser Arg Pro Ile Asp Ile Pro Pro
145                 150                 155                 160
```

Ala Pro Val Asp Gln Asn Val Ile Val Asp Ser Thr Gly Ala Leu Glu
            165                 170                 175

Phe Gln Ala Val Pro Lys Arg Leu Gly Val Ile Gly Ala Gly Val Ile
            180                 185                 190

Gly Leu Glu Leu Gly Ser Val Trp Ser Arg Leu Gly Ala Gln Val Thr
            195                 200                 205

Val Leu Glu Ala Leu Asp Thr Phe Leu Met Ala Ala Asp Thr Ala Val
            210                 215                 220

Ser Lys Glu Ala Leu Lys Thr Leu Thr Lys Gln Gly Leu Asp Ile Lys
225                 230                 235                 240

Leu Gly Ala Arg Val Thr Gly Ser Lys Val Asn Gly Glu Glu Val Val
            245                 250                 255

Val Thr Tyr Thr Asp Ala Asn Gly Glu Gln Thr Ile Thr Phe Asp Lys
            260                 265                 270

Leu Ile Val Ala Val Gly Arg Arg Pro Val Thr Thr Asp Leu Leu Ala
            275                 280                 285

Ala Asp Cys Gly Val Thr Leu Asp Glu Arg Gly Phe Val His Val Asp
            290                 295                 300

Asp His Cys Ala Thr Thr Val Pro Gly Val Tyr Ala Ile Gly Asp Val
305                 310                 315                 320

Val Arg Gly Met Met Leu Ala His Lys Ala Ser Glu Glu Gly Ile Met
            325                 330                 335

Val Ala Glu Arg Ile Lys Gly His Lys Ala Gln Met Asn Tyr Asp Leu
            340                 345                 350

Ile Pro Ser Val Ile Tyr Thr His Pro Glu Ile Ala Trp Val Gly Lys
            355                 360                 365

Thr Glu Gln Ala Leu Lys Ala Glu Gly Val Glu Val Asn Val Gly Thr
            370                 375                 380

Phe Pro Phe Ala Ala Ser Gly Arg Ala Met Ala Ala Asn Asp Thr Gly
385                 390                 395                 400

Gly Phe Val Lys Val Ile Ala Asp Ala Lys Thr Asp Arg Val Leu Gly
            405                 410                 415

Val His Val Ile Gly Pro Ser Ala Ala Glu Leu Val Gln Gln Gly Ala
            420                 425                 430

Ile Gly Met Glu Phe Gly Thr Ser Ala Glu Asp Leu Gly Met Met Val
            435                 440                 445

Phe Ser His Pro Thr Leu Ser Glu Ala Leu His Glu Ala Ala Leu Ala
450                 455                 460

Val Asn Gly Thr Ala Ile His Ile Ala Asn Arg Lys Lys Arg
465                 470                 475

<210> SEQ ID NO 9
<211> LENGTH: 1437
<212> TYPE: DNA
<213> ORGANISM: Unknown
<220> FEATURE:
<223> OTHER INFORMATION: DNA sequence encoding dihydrolipoamide
      dehydrogenase

<400> SEQUENCE: 9
atgactcaga aattcgacgt agtagtgatt ggcgcgggcc caggcggtta tgtagctgca    60
atcaaggcag cacagcttgg tctgacgact gcttgcatcg agaagtacac cgataaagag   120
ggcaagctgg ccctcggcgg tacttgcctg aacgtcggtt gcattccttc caaggcgctg   180
ctggacagct cctggaaatt ccatgaggcc caggacggtt cgccatcca cggtatcagc   240

-continued

```
cacgctggcg tgaccatgga cgtaccggcc atggtcggtc gcaaggccaa catcgtcaaa    300
ggcctgacca gcggtgttgc caccctgttc aaagccaacg gcgtaacctc gatccaaggc    360
cacggcaaac tgctggcagg caagaaagtc gaagtcacca agccggacgg ttcggttgaa    420
gtcatcgaag ctgaaaacgt gatcctggct ccaggttcgc gtccaatcga cattccaccg    480
gccccggtcg atcagaatgt catcgtcgac tccaccggcg cgctggaatt ccaggccgta    540
ccaaaacgtc tgggcgtgat cggcgctggc gttattggtc tggaactggg ctcggtctgg    600
tcgcgtctgg gcgcgcaagt gactgtcctg gaagccctgg acaccttcct gatggcagct    660
gacaccgctg tttccaagga agcgctgaaa accctgacca agcagggtct ggacatcaag    720
ctgggcgctc gcgtgaccgg ctccaaggtc aacggcgaag aagttgtggt gacctacacc    780
gacgccaacg gcgaacagac catcactttc gacaagctga ttgtcgccgt tggtcgccgt    840
ccggtgacca ccgatctgct ggctgccgac tgcggcgtga ctctcgacga gcgcggtttc    900
gtgcacgttg acgatcactg cgctactacc gtaccgggcg tctacgccat tggtgacgtg    960
gtgcgcggca tgatgctggc tcacaaggcc tcggaagagg gcatcatggt tgccgagcgc   1020
atcaagggcc acaaggccca gatgaactat gacctgatcc cttcggttat ctatactcac   1080
ccggaaattg catgggtcgg taaaaccgag caggccttga agctgaagg cgttgaagtt    1140
aacgtcggca cctttccgtt tgccgccagc ggccgtgcca tggcagccaa cgacaccggt   1200
ggtttcgtca aagtcatcgc cgatgccaag actgaccgcg tattgggcgt ccacgtgatt   1260
ggcccaagcg ctgcggaact ggttcagcaa ggtgcaatcg gcatggaatt cggcaccagc   1320
gccgaagacc tgggcatgat ggttttctct catccgaccc tgtccgaagc cctgcacgaa   1380
gcagctctgg ctgtgaatgg cactgccatc cacattgcca accgcaagaa acgctaa      1437
```